(12) United States Patent
Kim et al.

(10) Patent No.: US 8,748,175 B2
(45) Date of Patent: Jun. 10, 2014

(54) ANTIBODIES SPECIFICALLY BINDING TO THE EPIDERMAL GROWTH FACTOR RECEPTOR

(75) Inventors: Se-Ho Kim, Yongin-si (KR); Ki Hwan Chang, Yongin-si (KR); Kwang-Won Hong, Yongin-si (KR); Yong-Won Shin, Yongin-si (KR); Min-soo Kim, Yongin-si (KR); Hae-Won Lee, Yongin-si (KR); Yong Nam Shin, Yongin-si (KR); Kyung Hwan Ryoo, Yongin-si (KR); Dong Hyuck Seo, Yongin-si (KR); Jong-Hwa Won, Yongin-si (KR); Min-Kyu Hur, Yongin-si (KR)

(73) Assignee: Green Cross Corporation, Yongin-Si (KR)

( * ) Notice: Subject to any disclaimer, the term of this patent is extended or adjusted under 35 U.S.C. 154(b) by 44 days.

(21) Appl. No.: 13/499,155

(22) PCT Filed: Nov. 2, 2009

(86) PCT No.: PCT/KR2009/006380
§ 371 (c)(1),
(2), (4) Date: Mar. 29, 2012

(87) PCT Pub. No.: WO2011/040668
PCT Pub. Date: Apr. 7, 2011

(65) Prior Publication Data
US 2012/0231021 A1    Sep. 13, 2012

(30) Foreign Application Priority Data

Sep. 29, 2009  (KR) .................. 10-2009-0092401

(51) Int. Cl.
*C07K 16/28* (2006.01)
*C07K 16/30* (2006.01)
*C12N 15/13* (2006.01)
*C12N 5/10* (2006.01)
*C07K 14/71* (2006.01)

(52) U.S. Cl.
USPC ........... 435/358; 435/354; 435/363; 435/366; 435/320.1; 514/18.9; 514/19.2; 536/23.1; 536/23.53; 530/388.22; 530/388.8; 424/143.1; 424/155.1

(58) Field of Classification Search
None
See application file for complete search history.

(56) References Cited

U.S. PATENT DOCUMENTS

2002/0173629 A1    11/2002    Jakobovits et al.

FOREIGN PATENT DOCUMENTS

| WO | 98/24893 A2 | 6/1998 |
| WO | 02/30984 A1 | 4/2002 |
| WO | 02/100348 A2 | 12/2002 |
| WO | 2005/090407 A1 | 9/2005 |
| WO | 2009/030239 A1 | 3/2009 |

OTHER PUBLICATIONS del Pozo et al., Cycloheximide resistance as a yeast cloning marker, Curr. Genet. 19(5):353-358, May 1991.*
Heitner et al., "Selection of Cell Binding and Internalizing Epidermal Growth Factor Receptor Antibodies from a Phage Display Library," Journal of Immunological Methods, 2001, vol. 248, pp. 17-30.

(Continued)

*Primary Examiner* — Claire Kaufman
(74) *Attorney, Agent, or Firm* — Sughrue Mion, PLLC

(57) ABSTRACT

Provided are antibodies specifically binding to the epidermal growth factor receptor (EGFR) which are effective for the treatment of EGFR-mediated cancers.

30 Claims, 14 Drawing Sheets

(56) References Cited

OTHER PUBLICATIONS

Yang et al., "Eradication of Established Tumors by a Fully Human Monoclonal Antibody to the Epidermal Growth Receptor without Concomitant Chemotherapy," Cancer Research, 1999, vol. 59, pp. 1236-2343.

European Patent Office, European Search Report issued in corresponding EP Application No. 09850100.0, dated Jun. 17, 2013.

Zhou et al. "Impact of Single-chain FV Antibody Fragment Affinity on Nanoparticle Targeting of Epidermal Growth Factor Receptor-expressing Tumor Cells", Journal of Molecular Biology, 2007, 371(4): 934-947.

* cited by examiner

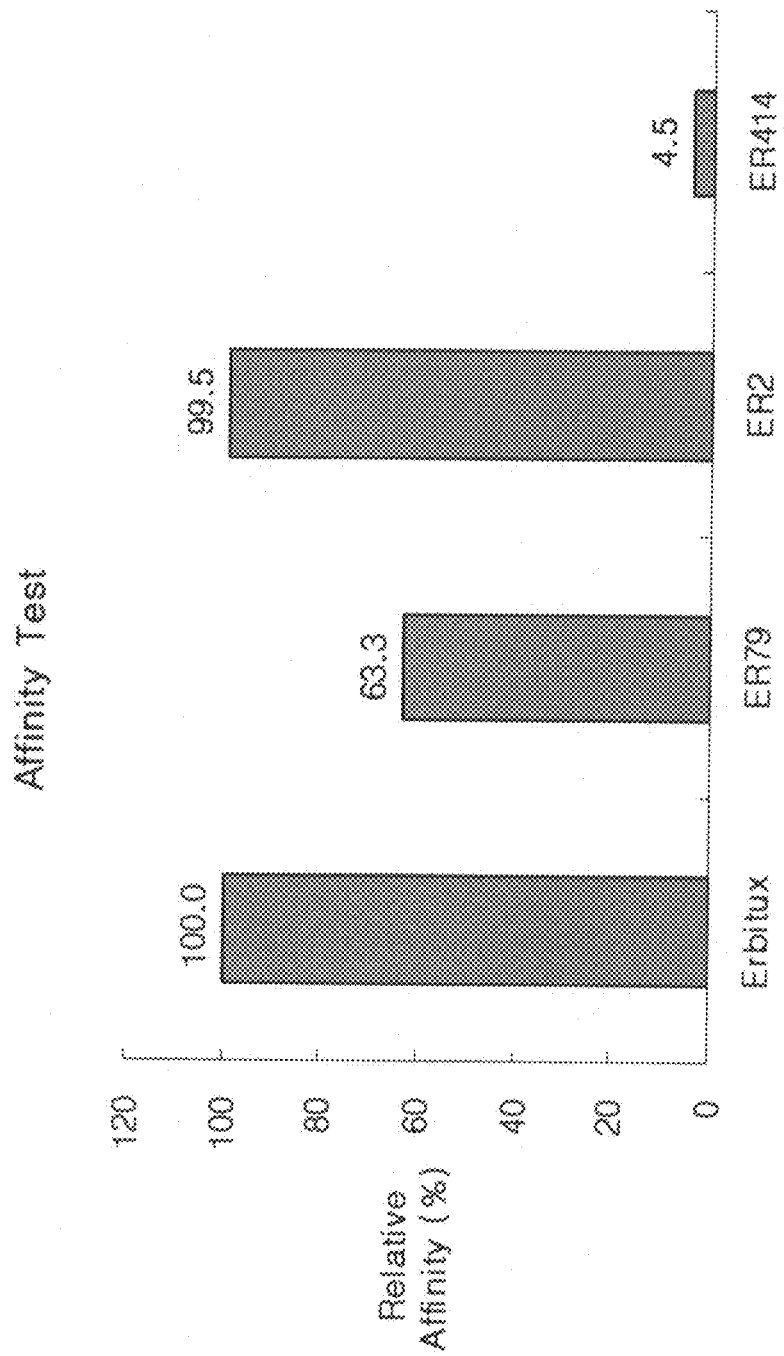

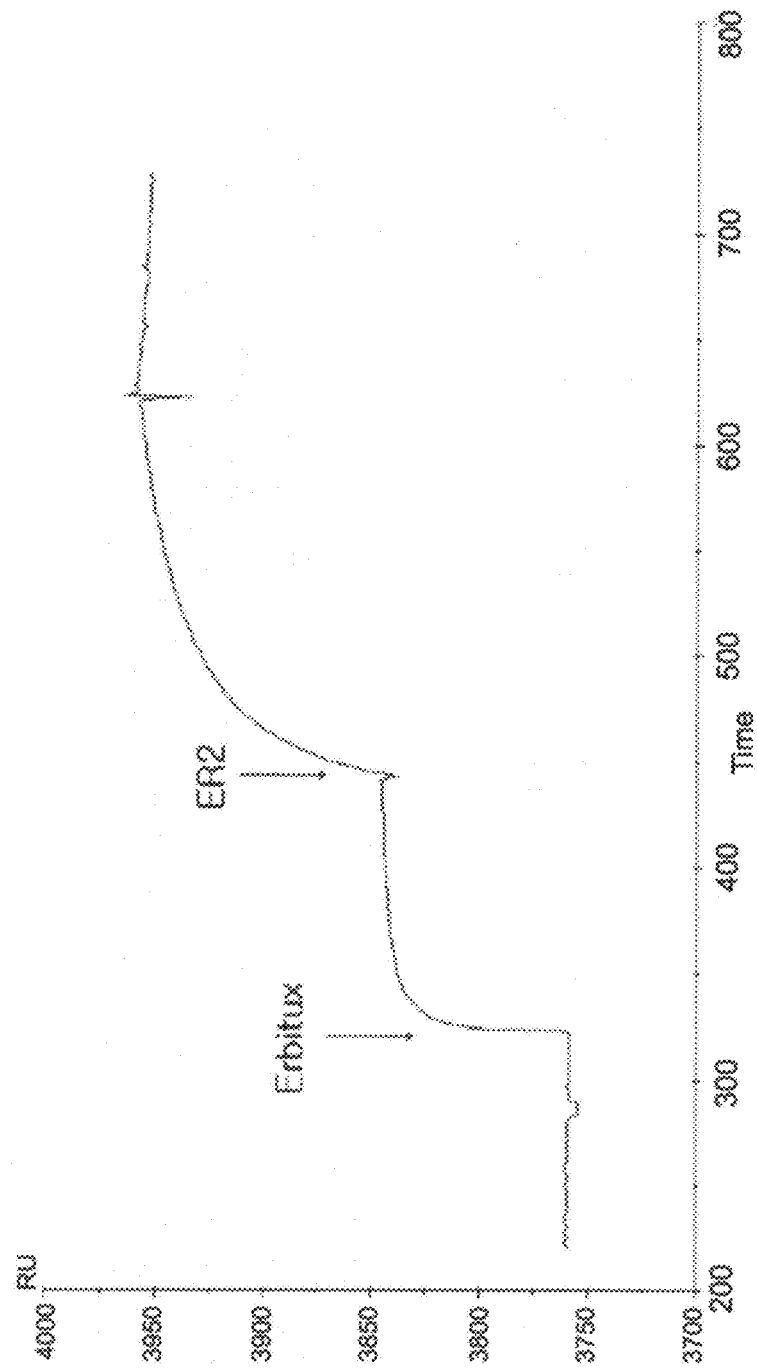

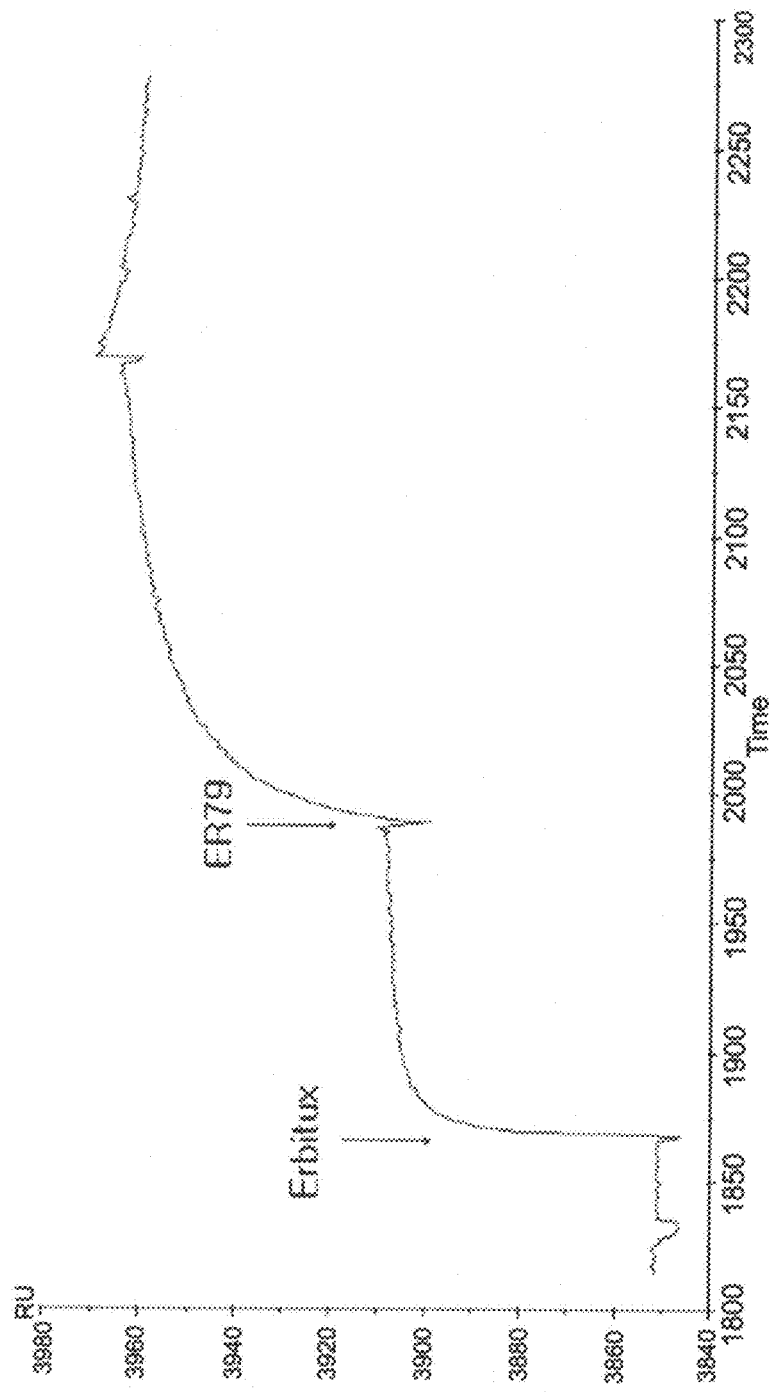

SEQUENCE LISTING

```
<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
<223> OTHER INFORMATION: Synthetic construct of CDR 1 of heavy chain
```

```
      variable region

<400> SEQUENCE: 1

Asp Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic construct of CDR 2 of heavy chain
      variable region

<400> SEQUENCE: 2

Gly Ile Leu Gly Gly Ser Glu Arg Ser Tyr Tyr Arg Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic construct of CDR 3 of heavy chain
      variable region

<400> SEQUENCE: 3

His Gly Ser Pro Gly Tyr Thr Leu Tyr Ala
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic construct of CDR 1 of light chain
      variable region

<400> SEQUENCE: 4

Arg Ser Asn Gln Asp Leu Thr His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic construct of CDR 2 of light chain
      variable region

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct of CDR 3 of light chain
      variable region

<400> SEQUENCE: 6

Met Gln Gly Thr His Trp Pro Trp Thr
1               5
```

```
<210> SEQ ID NO 7
<211> LENGTH: 122
<212> TYPE: PRT
<213> ORGANISM: Artificial Sequence
<220> FEATURE:
<223> OTHER INFORMATION: Synthetic construct of Heavy chain variable
      region

<400> SEQUENCE: 7

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Ser Asp Tyr
             20                  25                  30

Asp Met Ser Trp Ile Arg Gln Ala Pro Gly Lys Gly Leu Glu Trp Val
         35                  40                  45

Ser Gly Ile Leu Gly Gly Ser Glu Arg Ser Tyr Tyr Arg Asp Ser Val
     50                  55                  60

Lys Gly Arg Phe Thr Ile Ser Arg Asp Asn Ser Arg Lys Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Ser Pro Gly Tyr Thr Leu Tyr Ala Trp Asp Tyr Trp
            100                 105                 110

Gly Gln Gly Thr Thr Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Synthetic construct of Light chain variable
      region

<400> SEQUENCE: 8

Asp Ile Val Met Thr Gln Thr Pro Leu Ser Leu Pro Val Thr Pro Gly
 1               5                  10                  15

Glu Pro Ala Ser Ile Ser Cys Arg Ser Asn Gln Asp Leu Thr His Ser
             20                  25                  30

Asn Gly Asn Thr Tyr Leu Glu Trp Tyr Leu Gln Lys Pro Gly Gln Ser
         35                  40                  45

Pro Arg Leu Leu Ile Tyr Lys Val Ser Asn Arg Phe Ser Gly Val Pro
     50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Asp Ile Lys
            100                 105                 110

Arg

<210> SEQ ID NO 9
<211> LENGTH: 16
<212> TYPE: PRT
<213> ORGANISM: Artificial Sequence
<220> FEATURE:
<223> OTHER INFORMATION: Synthetic construct of CDR 1 of light chain
      variable region

<400> SEQUENCE: 9

Arg Ser Ser Gln Ser Val Asp Met Gly Ile Gly Asn Asn Tyr Leu Glu
```

```
                1               5                  10                 15
```

<210> SEQ ID NO 10
<211> LENGTH: 113
<212> TYPE: PRT
<213> ORGANISM: Artificial Sequence
<220> FEATURE:
<223> OTHER INFORMATION: Synthetic construct of Light chain variable
      region

<400> SEQUENCE: 10

Asp Ile Val Met Thr Gln Thr Pro Leu Ser Leu Pro Val Thr Pro Gly
 1               5                  10                  15

Glu Pro Ala Ser Ile Ser Cys Arg Ser Gln Ser Val Asp Met Gly
             20                  25                  30

Ile Gly Asn Asn Tyr Leu Glu Trp Tyr Leu Gln Lys Pro Gly Gln Ser
         35                  40                  45

Pro Arg Leu Leu Ile Tyr Lys Val Ser Asn Arg Phe Ser Gly Val Pro
     50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Asp Ile Lys
            100                 105                 110

Arg

<210> SEQ ID NO 11
<211> LENGTH: 15
<212> TYPE: DNA
<213> ORGANISM: Artificial Sequence
<220> FEATURE:
<223> OTHER INFORMATION: Synthetic construct of CDR 1 of heavy chain
      variable region

<400> SEQUENCE: 11
gactacgaca tgagc                                                         15

<210> SEQ ID NO 12
<211> LENGTH: 51
<212> TYPE: DNA
<213> ORGANISM: Artificial Sequence
<220> FEATURE:
<223> OTHER INFORMATION: Synthetic construct of CDR 2 of heavy chain
      variable region

<400> SEQUENCE: 12
gggatccttg gtggtagtga gcgttcgtac tatagggact ccgtgaaggg c                 51

<210> SEQ ID NO 13
<211> LENGTH: 39
<212> TYPE: DNA
<213> ORGANISM: Artificial Sequence
<220> FEATURE:
<223> OTHER INFORMATION: Synthetic construct of CDR 3 of heavy chain
      variable region

<400> SEQUENCE: 13
cacggcagcc cgggatacac gttgtatgcg tgggactac                               39

<210> SEQ ID NO 14
<211> LENGTH: 366
<212> TYPE: DNA
<213> ORGANISM: Artificial Sequence
<220> FEATURE:
<223> OTHER INFORMATION: Synthetic construct of Heavy chain variable
region

<400> SEQUENCE: 14

| gaggtgcagc tggtggagtc tgggggaggc gtggtacagc ctggagggtc cctgagactc | 60 |
| tcctgtgcag cctctggatt caccttcagt gactacgaca tgagctggat ccgccaggct | 120 |
| ccagggaagg gctggagtg gtctcaggg atccttggtg gtagtgagcg ttcgtactat | 180 |
| agggactccg tgaagggccg gttcaccatc tccagagaca attccaggaa aaccctgtat | 240 |
| ctgcaaatga cagcctgag agccgaggac acggctgtgt attactgtgc gagacacggc | 300 |
| agcccgggat acacgttgta tgcgtgggac tactggggcc aagggaccac ggtcaccgtc | 360 |
| tcctca | 366 |

<210> SEQ ID NO 15
<211> LENGTH: 48
<212> TYPE: DNA
<213> ORGANISM: Artificial Sequence
<220> FEATURE:
<223> OTHER INFORMATION: Synthetic construct of CDR 1 of light chain
variable region

<400> SEQUENCE: 15

| aggtctaatc aggacttgac ccatagtaac ggaaacacct atttggag | 48 |

<210> SEQ ID NO 16
<211> LENGTH: 21
<212> TYPE: DNA
<213> ORGANISM: Artificial Sequence
<220> FEATURE:
<223> OTHER INFORMATION: Synthetic construct of CDR 2 of light chain
variable region

<400> SEQUENCE: 16

| aaggtttcta accggttctc t | 21 |

<210> SEQ ID NO 17
<211> LENGTH: 27
<212> TYPE: DNA
<213> ORGANISM: Artificial Sequence
<220> FEATURE:
<223> OTHER INFORMATION: Synthetic construct of CDR 3 of light chain
variable region

<400> SEQUENCE: 17

| atgcaaggta cacactggcc gtggacg | 27 |

<210> SEQ ID NO 18
<211> LENGTH: 339
<212> TYPE: DNA
<213> ORGANISM: Artificial Sequence
<220> FEATURE:
<223> OTHER INFORMATION: Synthetic construct of Light chain variable
region

<400> SEQUENCE: 18

| gatattgtga tgacccagac tccactctcc ctgcccgtca cccctggaga gccggcctcc | 60 |
| atctcatgca ggtctaatca ggacttgacc catagtaacg gaaacaccta tttggagtgg | 120 |
| tacctgcaga agccagggca gtctccaaga ctcctaattt ataaggtttc taaccggttc | 180 |
| tctgtctcca agacaaccg gtgtggcagt ggggcaggta caaccgtcac actgagaatc | 240 |
| agcagggtgg aagctgagga tgttggggtt tattactgca tgcaaggtac acactggccg | 300 |

```
tggacgttcg gccaagggac caaggtggat atcaaacgt                339
```

<210> SEQ ID NO 19
<211> LENGTH: 48
<212> TYPE: DNA
<213> ORGANISM: Artificial Sequence
<220> FEATURE:
<223> OTHER INFORMATION: Synthetic construct of CDR 1 of light chain variable region

<400> SEQUENCE: 19

```
aggtctagtc agagcgtcga catggggatc ggaaacaact atttggag      48
```

<210> SEQ ID NO 20
<211> LENGTH: 339
<212> TYPE: DNA
<213> ORGANISM: Artificial Sequence
<220> FEATURE:
<223> OTHER INFORMATION: Synthetic construct of Light chain variable region

<400> SEQUENCE: 20

```
gatattgtga tgacccagac tccactctcc ctgcccgtca cccctggaga gccggcctcc    60
atctcatgca ggtctagtca gagcgtcgac atggggatcg aaacaacta tttggagtgg   120
tacctgcaga agccagggca gtctccaaga ctcctaattt ataaggtttc taaccggttc   180
tctggggtcc cagacagatt cagtggcagt ggggcaggta cagatttcac actgagaatc   240
agcagggtgg aagctgagga tgttgggggtt tattactgca tgcaaggtac acactggccg   300
tggacgttcg gccaagggac caaggtggat atcaaacgt                         339
```

<210> SEQ ID NO 21
<211> LENGTH: 36
<212> TYPE: DNA
<213> ORGANISM: Artificial Sequence
<220> FEATURE:
<223> OTHER INFORMATION: scFv-forward primer

<400> SEQUENCE: 21

```
gttgttcctt tctatgcggc ccagccggcc atggcc                  36
```

<210> SEQ ID NO 22
<211> LENGTH: 30
<212> TYPE: DNA
<213> ORGANISM: Artificial Sequence
<220> FEATURE:
<223> OTHER INFORMATION: scFv-reverse primer

<400> SEQUENCE: 22

```
gagtcattct cgacttgcgg ccgcacgttt                         30
```

<210> SEQ ID NO 23
<211> LENGTH: 27
<212> TYPE: DNA
<213> ORGANISM: Artificial Sequence
<220> FEATURE:
<223> OTHER INFORMATION: scFv-reverse primer

<400> SEQUENCE: 23

```
gagtcattct cgacttgcgg ccgcacc                            27
```

<210> SEQ ID NO 24
<211> LENGTH: 39
<212> TYPE: DNA
<213> ORGANISM: Artificial Sequence
<220> FEATURE:

<223> OTHER INFORMATION: VH1-forward primer

<400> SEQUENCE: 24
cagccggcca tggcccaggt gcagctggtg cagtctggg          39

<210> SEQ ID NO 25
<211> LENGTH: 39
<212> TYPE: DNA
<213> ORGANISM: Artificial Sequence
<220> FEATURE:
<223> OTHER INFORMATION: VH3-forward primer

<400> SEQUENCE: 25
cagccggcca tggccsaggt gcagctggtg gagtctggg          39

<210> SEQ ID NO 26
<211> LENGTH: 39
<212> TYPE: DNA
<213> ORGANISM: Artificial Sequence
<220> FEATURE:
<223> OTHER INFORMATION: VH4-forward primer

<400> SEQUENCE: 26
cagccggcca tggcccaggt gcagctgcag gagtcgggc          39

<210> SEQ ID NO 27
<211> LENGTH: 45
<212> TYPE: DNA
<213> ORGANISM: Artificial Sequence
<220> FEATURE:
<223> OTHER INFORMATION: VH-reverse primer

<400> SEQUENCE: 27
cgatccgcca cctccggagc cacctccgcc tgaaccgcct ccacc          45

<210> SEQ ID NO 28
<211> LENGTH: 48
<212> TYPE: DNA
<213> ORGANISM: Artificial Sequence
<220> FEATURE:
<223> OTHER INFORMATION: VK1/3A-forward primer

<400> SEQUENCE: 28
ggtggctccg gaggtggcgg atcggacatc cagatgaccc agtctcca          48

<210> SEQ ID NO 29
<211> LENGTH: 48
<212> TYPE: DNA
<213> ORGANISM: Artificial Sequence
<220> FEATURE:
<223> OTHER INFORMATION: VK1/3B-forward primer

<400> SEQUENCE: 29
ggtggctccg gaggtggcgg atcggaaatt gtgttgacgc agtctcca          48

<210> SEQ ID NO 30
<211> LENGTH: 51
<212> TYPE: DNA
<213> ORGANISM: Artificial Sequence
<220> FEATURE:
<223> OTHER INFORMATION: VK2-forward primer

<400> SEQUENCE: 30
ggtggctccg gaggtggcgg atcggatatt gtgatgaccc agactccact c          51

<210> SEQ ID NO 31

```
<211> LENGTH: 39
<212> TYPE: DNA
<213> ORGANISM: Artificial Sequence
<220> FEATURE:
<223> OTHER INFORMATION: JK_A-reverse primer

<400> SEQUENCE: 31
tcgacttgcg gccgcacgtt tgatwtccac yttggtccc                              39

<210> SEQ ID NO 32
<211> LENGTH: 39
<212> TYPE: DNA
<213> ORGANISM: Artificial Sequence
<220> FEATURE:
<223> OTHER INFORMATION: JK_B-reverse primer

<400> SEQUENCE: 32
tcgacttgcg gccgcacgtt tgatctccas cttggtccc                              39

<210> SEQ ID NO 33
<211> LENGTH: 39
<212> TYPE: DNA
<213> ORGANISM: Artificial Sequence
<220> FEATURE:
<223> OTHER INFORMATION: JK_C-reverse primer

<400> SEQUENCE: 33
tcgacttgcg gccgcacgtt taatctccag tcgtgtccc                              39

<210> SEQ ID NO 34
<211> LENGTH: 48
<212> TYPE: DNA
<213> ORGANISM: Artificial Sequence
<220> FEATURE:
<223> OTHER INFORMATION: VL_A-forward primer

<400> SEQUENCE: 34
ggtggctccg gaggtggcgg atcgcagtct gysctgactc agccaccc                    48

<210> SEQ ID NO 35
<211> LENGTH: 48
<212> TYPE: DNA
<213> ORGANISM: Artificial Sequence
<220> FEATURE:
<223> OTHER INFORMATION: VL_B-forward primer

<400> SEQUENCE: 35
ggtggctccg gaggtggcgg atcgtcctat gagctgacwc agccaccc                    48

<210> SEQ ID NO 36
<211> LENGTH: 42
<212> TYPE: DNA
<213> ORGANISM: Artificial Sequence
<220> FEATURE:
<223> OTHER INFORMATION: JL_A-reverse primer

<400> SEQUENCE: 36
ttctcgactt gcggccgcac ctaggacggt sascttggtc cc                          42

<210> SEQ ID NO 37
<211> LENGTH: 42
<212> TYPE: DNA
<213> ORGANISM: Artificial Sequence
<220> FEATURE:
<223> OTHER INFORMATION: JL_B-reverse primer

<400> SEQUENCE: 37
```
ttctcgactt gcggccgcac cgaggacggt cagctgggtg cc                    42

<210> SEQ ID NO 38
<211> LENGTH: 24
<212> TYPE: DNA
<213> ORGANISM: Artificial Sequence
<220> FEATURE:
<223> OTHER INFORMATION: P033 sequencing primer

<400> SEQUENCE: 38
caacgtgaaa aaattattat tcgc                                        24

<210> SEQ ID NO 39
<211> LENGTH: 60
<212> TYPE: DNA
<213> ORGANISM: Artificial Sequence
<220> FEATURE:
<223> OTHER INFORMATION: VH-forward primer

<400> SEQUENCE: 39
ggagacccaa gcttggtacc gagctcggat ccactagtaa cggccgccag tgtgctggaa    60

<210> SEQ ID NO 40
<211> LENGTH: 42
<212> TYPE: DNA
<213> ORGANISM: Artificial Sequence
<220> FEATURE:
<223> OTHER INFORMATION: VH-reverse primer

<400> SEQUENCE: 40
gaagaccgat gggcccttgg tggaggctga ggagacggtg ac                    42

<210> SEQ ID NO 41
<211> LENGTH: 45
<212> TYPE: DNA
<213> ORGANISM: Artificial Sequence
<220> FEATURE:
<223> OTHER INFORMATION: VL-forward primer

<400> SEQUENCE: 41
tagggagacc cgctagcgga gcaagatgga ttcacaggcc caggt                 45

<210> SEQ ID NO 42
<211> LENGTH: 45
<212> TYPE: DNA
<213> ORGANISM: Artificial Sequence
<220> FEATURE:
<223> OTHER INFORMATION: VL-reverse primer

<400> SEQUENCE: 42
tatagaatag ggcccccccct cgaggtcgac ctaacactct cccct                45

<210> SEQ ID NO 43
<211> LENGTH: 330
<212> TYPE: PRT
<213> ORGANISM: Artificial Sequence
<220> FEATURE:
<223> OTHER INFORMATION: Synthetic construct of Heavy chain constant
      region

<400> SEQUENCE: 43

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser

```
                    35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
                130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 44
<211> LENGTH: 106
<212> TYPE: PRT
<213> ORGANISM: Artificial Sequence
<220> FEATURE:
<223> OTHER INFORMATION: Synthetic construct of Light chain constant
      region

<400> SEQUENCE: 44

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
                20                  25                  30
Pro Arg Glu Ala Lys Val Gln Trp Lys Val Asp Asn Ala Leu Gln Ser
                35                  40                  45
Gly Asn Ser Gln Glu Ser Val Thr Glu Gln Asp Ser Lys Asp Ser Thr
                50                  55                  60
Tyr Ser Leu Ser Ser Thr Leu Thr Leu Ser Lys Ala Asp Tyr Glu Lys
```

-continued

```
             65                  70                  75                  80
His Lys Val Tyr Ala Cys Glu Val Thr His Gln Gly Leu Ser Ser Pro
                     85                  90                  95

Val Thr Lys Ser Phe Asn Arg Gly Glu Cys
            100                 105
```

ANTIBODIES SPECIFICALLY BINDING TO THE EPIDERMAL GROWTH FACTOR RECEPTOR

CROSS REFERENCE TO RELATED APPLICATIONS

This application is a National Stage of International Application No. PCT/KR2009/006380 filed Nov. 2, 2009, claiming priority based on Korean Patent Application No. 10-2009-0092401 filed Sep. 29, 2009, the contents of all of which are incorporated herein by reference in their entirety.

FIELD OF THE INVENTION

The present invention relates to antibodies specifically binding to the epidermal growth factor receptor (EGFR).

BACKGROUND OF THE INVENTION

The epidermal growth factor receptor (EGFR) is a 170 kDa type I transmembrane protein and is known to be overexpressed in many human tumors, e.g., carcinoma of the lung, breast, colon, stomach, brain, bladder, head, neck, ovaries and prostate. Its overexpression is frequently accompanied by the production of EGFR-ligands, TGF-α (transforming growth factor-α) and EGF (epidermal growth factor), and the binding of the ligands to EGFR was confirmed to induce cell proliferation and tumor growth. Blocking the interaction between such ligands and EGFR using an antibody against EGFR therefore can inhibit tumor growth, which has been proven effective by experiments that employed monoclonal antibodies against EGFR.

Antibody C225 (trade name: Erbitux; ImClone, U.S), which is currently used in clinical trials for the treatment of metastatic colorectal cancers, is a chimeric antibody, comprising the mouse antibody variable regions linked to human antibody IgG1 constant regions (about 30% of mouse amino acid sequence is included therein). C225 has been shown to inhibit tumor cell growth, EGFR phosphorylation in vitro and tumor formation in a nude mouse, and also to completely eradicate human tumor xenografts in mice when used together with a specific chemotherapeutic agent. However, the antibody has the problem of inducing immune reactions in some (~10%) of the patients treated therewith. Accordingly, there exists a need for improved therapeutic antibodies against EGFR.

Therapeutic agents for target therapy constitute about 50% of anticancer drugs recently approved by U.S. Food and Drug Administration (FDA). Such antibodies provide target specificity and a capability to effectively engage the immune system, which in combination with long biological half-lives thereof have alerted researchers to the therapeutic potentials thereof. As a result, the U.S. FDA has recently approved the use of several antibodies for cancer treatment. Antibodies play prominent roles in many therapeutic approaches to diseases, which has become even more attractive with the recent advent of technologies that allow the development of fully human antibodies.

The present inventors have endeavored to develop novel, improved antibodies having new complementarity determining regions (CDRs) and have found that such antibodies can be used in cancer treatment by blocking the EGFR-mediated signal transduction.

SUMMARY OF THE INVENTION

Therefore, it is an object of the present invention to provide a novel antibody which specifically binds to the epidermal growth factor receptor.

It is another object of the present invention to provide DNAs which respectively encode the heavy chain variable region and the light chain variable region of said antibody, and an expression vector comprising the same.

It is still another object of the present invention to provide a cell line transformed with the expression vector.

It is a further object of the present invention to provide a pharmaceutical composition for treating a cancer, comprising said antibody.

In accordance with one aspect of the present invention, there is provided an antibody specifically binding to the epidermal growth factor receptor (EGFR), comprising: a) a heavy chain variable region comprising complementarity determining regions (CDRs) 1, 2, and 3 having the amino acid sequences of SEQ ID NOs: 1, 2, and 3, respectively; b) a light chain variable region comprising CDR 1, CDR 2, and CDR 3 having the amino acid sequences of SEQ ID NOs: 4, 5, and 6, respectively; c) a heavy chain constant region; and d) a light chain constant region.

Further, there is provided an antibody specifically binding to the epidermal growth factor receptor (EGFR), comprising: a) a heavy chain variable region comprising CDR 1, CDR 2, and CDR 3 having the amino acid sequences of SEQ ID NOs: 1, 2, and 3, respectively; b) a light chain variable region comprising CDR 1, CDR 2, and CDR 3 having the amino acid sequences of SEQ ID NOs: 9, 5, and 6, respectively; c) a heavy chain constant region; and d) a light chain constant region.

In accordance with another aspect of the present invention, there is provided a DNA encoding the heavy chain variable region or the light chain variable region of the antibody, and an expression vector comprising the same.

In accordance with a still another aspect of the present invention, there is provided a cell line transformed with said expression vector.

In accordance with a further aspect of the present invention, there is provided a composition for treating a cancer, comprising said antibody.

BRIEF DESCRIPTION OF THE DRAWINGS

The above and other objects and features of the present invention will become apparent from the following description of the invention, when taken in conjunction with the accompanying drawings, which respectively show:

FIG. 12: surface plasmon resonance measurement results revealing the binding sites of the inventive antibodies with the epidermal growth factor, and those of chimeric antibody C225 (Erbitux).

DETAILED DESCRIPTION OF THE INVENTION

Hereinafter, the present invention is described in detail.

The present invention provides an antibody specifically binding to the epidermal growth factor receptor (EGFR), comprising a) a heavy chain variable region comprising complementarity determining regions (CDRs) 1, 2, and 3 having the amino acid sequences of SEQ ID NOs: 1, 2, and 3, respectively; b) a light chain variable region comprising CDR 1, CDR 2, and CDR 3 having the amino acid sequences of SEQ ID NOs: 4, 5, and 6, respectively; c) a heavy chain constant region; and d) a light chain constant region. Preferably, the antibody may be one, comprising: a) a heavy chain variable region having the amino acid sequence of SEQ ID NO:7; b) a light chain variable region having the amino acid sequence of SEQ ID NO:8; c) a heavy chain constant region; and d) a light chain constant region.

Further, the present invention provides an antibody specifically binding to the epidermal growth factor receptor (EGFR), comprising: a) a heavy chain variable region comprising CDR 1, CDR 2, and CDR 3 having the amino acid sequences of SEQ ID NOs: 1, 2, and 3, respectively; b) a light chain variable region comprising CDR 1, CDR 2, and CDR 3 having the amino acid sequences of SEQ ID NOs: 9, 5, and 6, respectively; c) a heavy chain constant region; and d) a light chain constant region. Preferably, the antibody may be one, comprising: a) a heavy chain variable region having the amino acid sequence of SEQ ID NO:7; b) a light chain variable region having the amino acid sequence of SEQ ID No:10; c) a heavy chain constant region; and d) a light chain constant region.

The inventive antibodies may be preferably human antibodies, and is characterized in blocking the signal transduction induced by the epidermal growth factor (EGF).

The antibodies specifically binding to the epidermal growth factor receptor may be preferably selected by a modification of a phage display method (Smith, *Science*, 228, 1315-1317, 1985; and Hoogenboom & Chames, *Immunol Today*, 21, 371-378, 2000). In the phage display method, a gene (gene III) encoding a surface protein of filamentous phage (e.g. M13, Fd or F1) is fused with a gene encoding an antibody of interest, thereby virus particles having the fused antibody exposed on the surface is produced as an antibody-phage form. Subsequently, an antibody of interest can be selected from a phage library through the biopanning technique using high specificity and affinity of the antibody and high infective property of the phage (Burton & Barbas, *Adv. Immunol.*, 57, 191-280, 1994; Winter et al., *Annu. Rev. Immunol.*, 12, 433-455, 1994; and Hoogenboom et al., *Immunotechnology*, 4, 1-20, 1998). The phage display vector may be pKS4H (see Korean Patent no. 0635370) or pCANTAB5E, preferably, pKS4H.

Figure 9A:
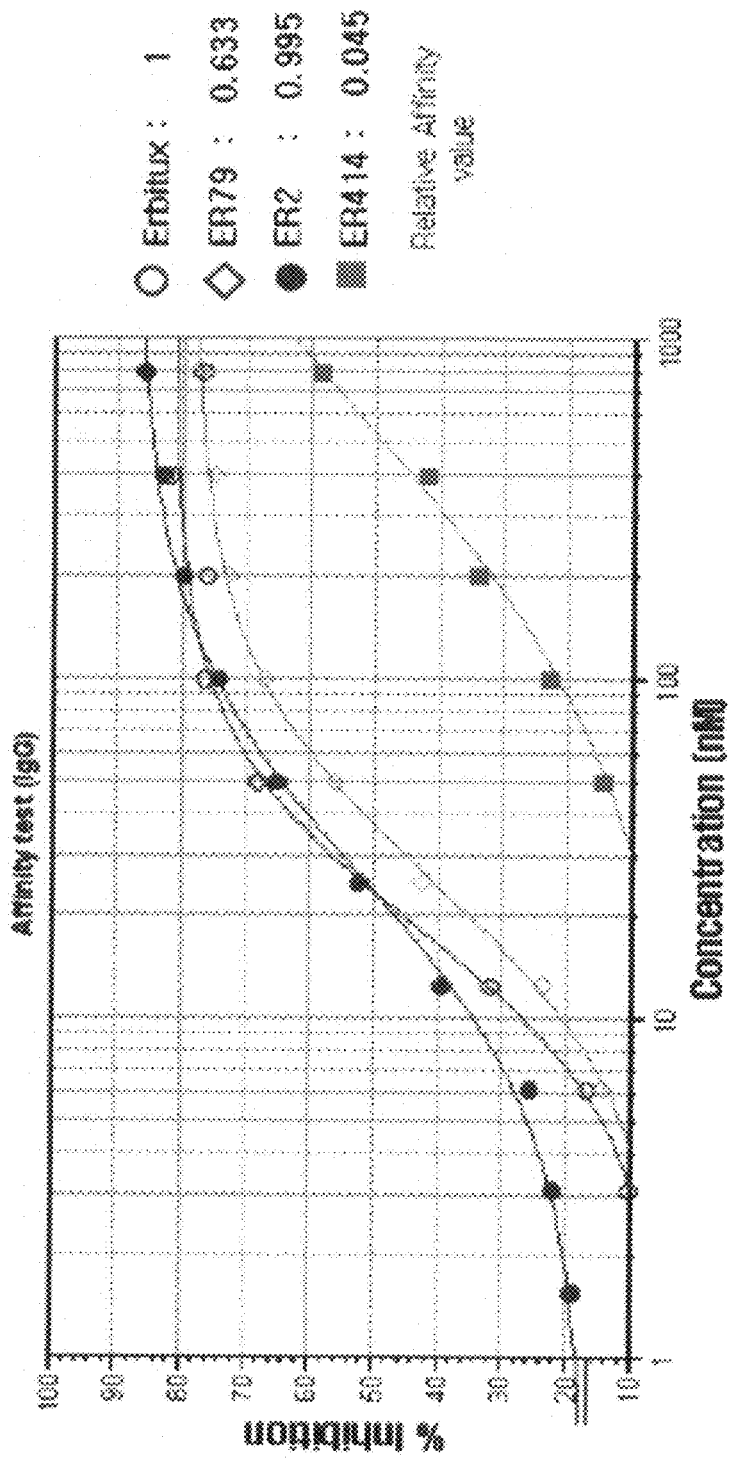
FIG. 9: relative affinities of the human antibodies (ER2 and ER79), a chimeric antibody (C225, Erbitux), and other antibody (ER414) to the epidermal growth factor receptor.
Figure 11:
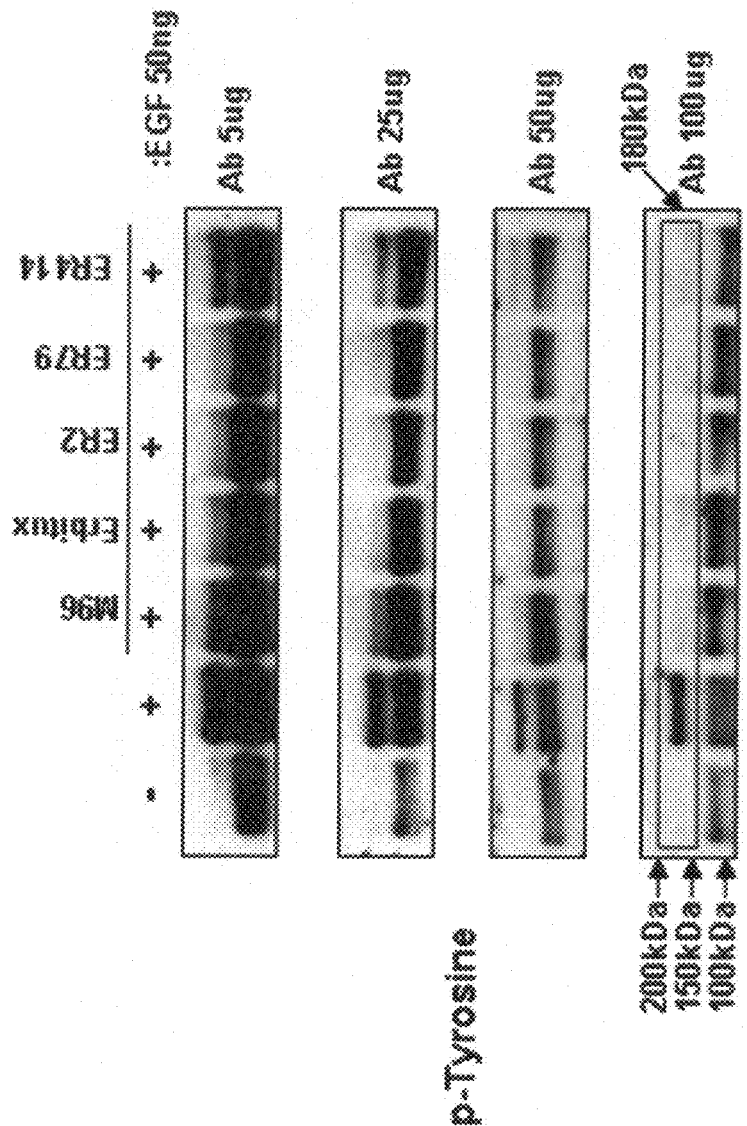
FIG. 11: the inhibitory effect of the inventive antibodies on the phosphorylation of the epidermal growth factor receptor.

In the present invention, a human antibody ER414 was selected from a phage library and its affinity and neutralizing power against the epidermal growth factor receptor were checked (FIGS. 9 and 11). The ER414 antibody has the neutralizing power, but its affinity was 16 times lower than commercially available antibody, C225. Accordingly, improved antibodies with similar affinities were selected using the affinity maturation process. That is, a library was generated through the amino acid randomization of complementarity determining regions of the antibody primarily selected, antibodies having the affinity matured were selected using biopanning technique, and finally antibodies (ER2 and ER79) having similar affinities to C225 antibody were selected by the competitive ELISA method.

In case of the antibody ER2, CDR 1, CDR 2, and CDR 3 of the heavy chain variable region have the amino acid sequences of SEQ ID NOs: 1, 2, and 3, respectively, and CDR 1, CDR 2, and CDR 3 of the light chain variable region have the amino acid sequences of SEQ ID NOs: 4, 5, and 6, respectively, as a result of sequence analysis. On the other hand, CDR 1, CDR 2, and CDR 3 of the heavy chain variable region of the antibody ER79 have the amino acid sequences of SEQ ID NOs: 1, 2, and 3, respectively, and CDR 1, CDR 2, and CDR 3 of the light chain variable region have the amino acid sequences of SEQ ID NOs: 9, 5, and 6, respectively.

The heavy chain constant regions or light chain constant regions of the inventive antibodies may be identical to those of a human antibody, and may be preferably amino acids having the amino acid sequences of SEQ ID NOs: 43 and 44, respectively.

The present invention provides a DNA encoding an antibody heavy chain variable region comprising CDR 1, CDR 2, and CDR 3 having the amino acid sequences of SEQ ID NOs: 1, 2, and 3, respectively. Preferably, the DNA may comprise the polynucleotide having the nucleotide sequence of SEQ ID NO: 11 encoding the amino acid sequence of SEQ ID NO: 1, the polynucleotide having the nucleotide sequence of SEQ ID NO: 12 encoding the amino acid sequence of SEQ ID NO: 2 and the polynucleotide having the nucleotide sequence of SEQ ID NO: 13 encoding the amino acid sequence of SEQ ID NO: 3.

The present invention provides a DNA encoding an antibody heavy chain variable region having the amino acid sequence of SEQ ID NO: 7. Preferably, the DNA may comprise the polynucleotide having the nucleotide sequence of SEQ ID NO: 14 encoding the amino acid sequences of SEQ ID NO: 7.

Further, the present invention provides a DNA encoding an antibody light chain variable region comprising CDR 1, CDR 2, and CDR 3 having the amino acid sequences of SEQ ID NOs: 4, 5, and 6, respectively. Preferably, the DNA may comprise the polynucleotide having the nucleotide sequence of SEQ ID NO: 15 encoding the amino acid sequence of SEQ ID NO: 4, the polynucleotide having the nucleotide sequence of SEQ ID NO: 16 encoding the amino acid sequence of SEQ ID NO: 5, and the polynucleotide having the nucleotide sequence of SEQ ID NO: 17 encoding the amino acid sequence of SEQ ID NO: 6.

The present invention provides a DNA encoding an antibody light chain variable region having the amino acid sequences of SEQ ID NO: 8. Preferably, the DNA may comprise the polynucleotide having the nucleotide sequence of SEQ ID NO: 18 encoding the amino acid sequences of SEQ ID NO: 8.

Further, the present invention provides a DNA encoding an antibody light chain variable region comprising CDR 1, CDR 2, and CDR 3 having the amino acid sequences of SEQ ID NOs: 9, 5, and 6, respectively. Preferably, the DNA may comprise the polynucleotide having the nucleotide sequence of SEQ ID NO: 19 encoding the amino acid sequence of SEQ ID NO: 9, the polynucleotide having the nucleotide sequence of SEQ ID NO: 16 encoding the amino acid sequence of SEQ ID NO: 5 and the polynucleotide having the nucleotide sequence of SEQ ID NO: 17 encoding the amino acid sequence of SEQ ID NO: 6.

The present invention provides a DNA encoding an antibody light chain variable region having the amino acid sequences of SEQ ID NO: 10. Preferably, the DNA may comprise the polynucleotide having the nucleotide sequence of SEQ ID NO: 20 encoding the amino acid sequences of SEQ ID NO: 10.

Figure 5:
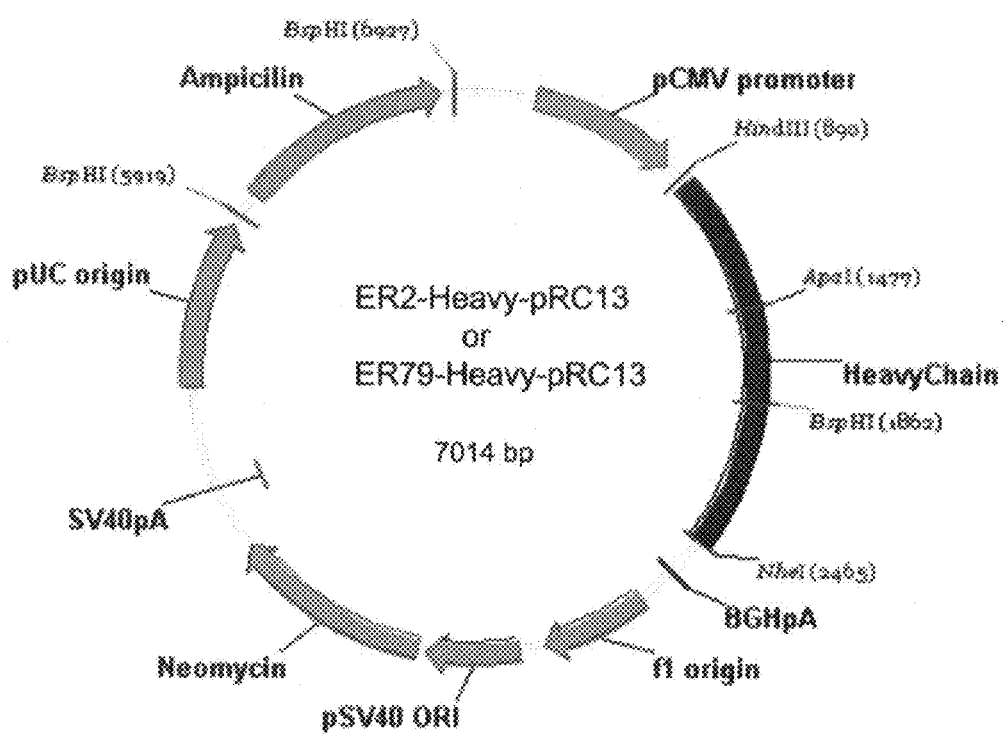
FIG. 5: a cleavage map of the expression vector for expressing the heavy chain of the human antibody of the present invention, ER2-Heavy-pRC13 or ER79-Heavy-pRC13.

The present invention provides an expression vector for expressing the heavy chain variable region of the antibody specifically binding to the epidermal growth factor receptor (EGFR), comprising the DNA encoding the heavy chain variable region of the antibody. Preferably, the expression vector may be "ER2-Heavy-pRC13" or "ER79-Heavy-pRC13" whose cleavage map is shown in FIG. 5.

Specifically, the vector may be prepared by inserting the VH fragment (1-a: ER2Ab-H or 1-b: ER79Ab-H) of the antibody selected using panning and affinity maturation processes into a suitable vector, e.g., pRC13 vector (deposit No. KCLRF-BP-00054; Korean Patent No. 523732).

Figure 6:
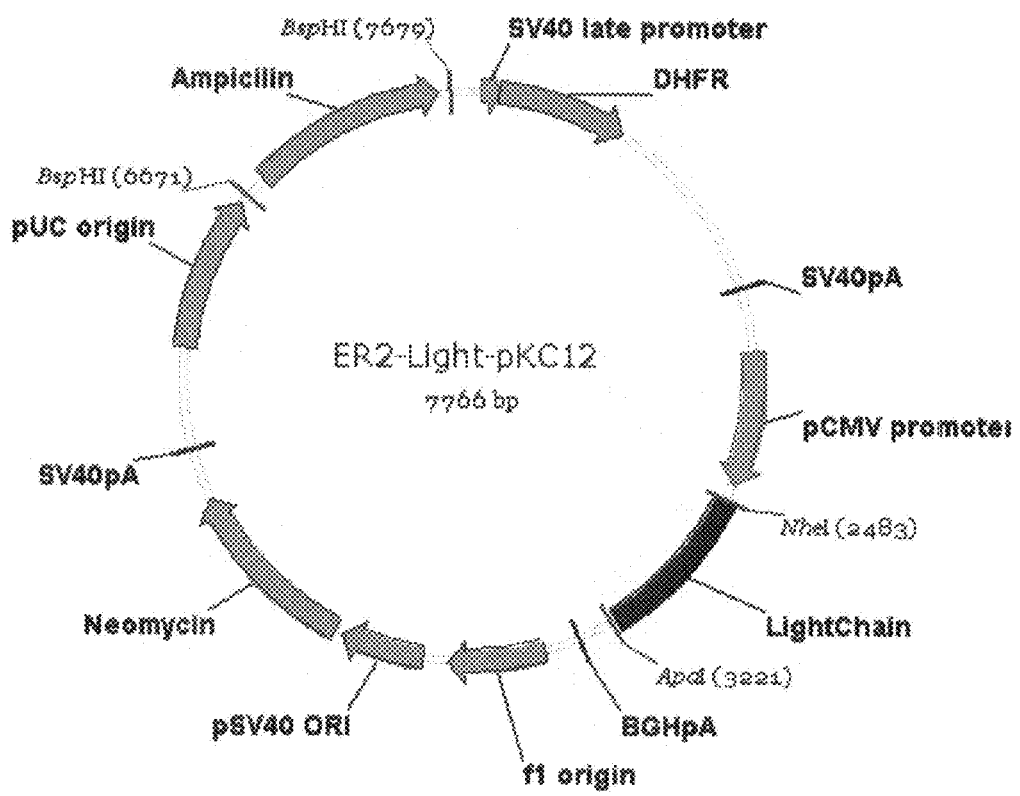
FIGS. 6 and 7: cleavage maps of expression vectors for expressing the light chains of the human antibodies of the present invention, ER2-Light-pKC12 and ER79-Light-pKC12.
Figure 7:
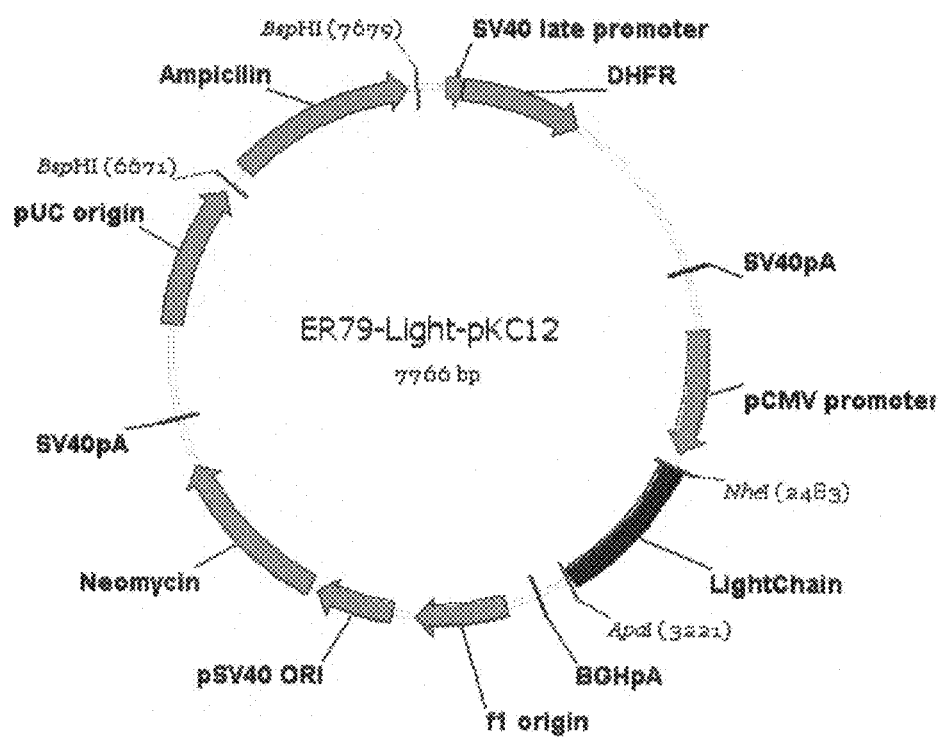

The present invention provides an expression vector for expressing the light chain variable region of the antibody specifically binding to the epidermal growth factor receptor (EGFR), comprising the DNA encoding the light chain variable region of the antibody. Preferably, the expression vector may be "ER2-Light-pKC12" whose cleavage map is shown in FIG. 6, or "ER79-Light-pKC12" whose cleavage map is shown in FIG. 7.

Specifically, the vectors may be prepared by inserting each VL fragment (2-a: ER2Ab-L or 1-b: ER79Ab-L) of the antibodies selected using the panning and affinity maturation processes into a suitable vector, e.g., pKC12 vector (deposit No. KCLRF-BP-00054; Korean Patent No. 523732).

The present invention provides an animal cell line transformed with the expression vector for expressing the heavy chain variable region of the inventive antibody, and the expression vector for expressing the light chain variable region of the inventive antibody. The expression vector for expressing the heavy chain variable region of the inventive antibody may be preferably ER2-Heavy-pRC13, or ER79-Heavy-pRC13, and the expression vector for expressing the light chain variable region of the inventive antibody may be preferably ER2-Light-pKC12, or ER79-Light-pKC12. The animal cell line may be CHO (Chinese hamster ovary), HEK 293, or NSO cell line, preferably, CHO (Chinese hamster ovary) cell line.

The antibodies according to the present invention may be prepared by which the heavy chain variable region and the light chain variable region are combined together.

The affinity of the inventive antibodies to the antigen may be measured, e.g., by the competitive ELISA (Kim et al., *Hybridoma*, 20, 265-272, 2001). As shown in FIG. 9, the affinity of ER2 antibody of the present invention is similar to that of C225 antibody, whereas the affinity of ER79 antibody is two times lower than that of C225 antibody. Further, the antibodies was demonstrated to bind to the epidermal growth factor receptor overexpressed in a cancer cell line using a flow cytometer (FACS) (FIG. 10), and confirmed to have the neutralizing power through the experiment of the epidermal growth factor receptor phosphorylation inhibition in a breast cancer cell (FIG. 11). Therefore, the antibodies of the present invention may be used as an antibody for treating a cancer by inhibiting the signal transduction through the epidermal growth factor receptor.

In view of the result, the present invention provides a composition, preferably pharmaceutical composition, for treating a cancer, comprising the antibody. The composition may further comprise at least one selected from the group consisting of cisplatin, gemcitabine, doxorubicin, 5-FU, irrinotecan, and paclitaxel.

The composition contains ER2 or ER79 antibody or transformants containing the same as an active ingredient and additionally includes one or more effective ingredients having the same or similar functions to the said active ingredient. In addition to the active ingredient, the composition of the present invention can include one or more pharmaceutically acceptable carriers such as saline, sterilized water, Ringer's solution, buffered saline, dextrose solution, maltodextrin solution, glycerol, ethanol, liposome and a mixture comprising one or more of those components. If necessary, a general additive such as an antioxidant, a buffer, and a bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. A target cell specific antibody or other ligands can be mixed with one of the said carriers to be delivered to the target cell. The composition can further be prepared in suitable forms according to ingredients by following the method represented in Remington's Pharmaceutical Science, Mack Publishing Company, Easton Pa.

The pharmaceutical composition of the present invention can be administered parenterally (for example, intravenous, hypodermic, peritoneal or local injection), and intravenous injection is preferred. In some cases of solid cancer, local administration which favors fast and easy access of antibody is more preferred. The effective dosage of the composition can be determined according to weight, age, gender, health condition, diet, administration frequency, administration method, excretion and severity of a disease. One time dosage of the composition containing humanized antibody or transformant approximately 5-500 mg/m$^2$, which can be administered daily or weekly. The effective dosage can be adjusted by a doctor who treats malignant tumor patients.

The pharmaceutical composition of the present invention can be administered alone or together with surgical operation, hormone therapy, chemo-therapy and biological regulators to treat malignant tumors.

The following Examples are given for the purpose of illustration only, and are not intended to limit the scope of the invention.

EXAMPLE 1

Isolation of RNA

In order to select antibodies specifically binding to the epidermal growth factor receptor, a gene library of antibodies was constructed. Human bone marrow total RNA, human thymus total RNA, human spleen total RNA and human B cell RNA were used as a mix. All RNAs except for human B cell RNA were purchased from Clontech (U.S) and human B cell RNA was isolated as follows:

50 mL of blood taken from a healthy adult was diluted by mixing with 50 mL of HBSS (Hank's balanced salt solution; Sigma, US) in a mixing ratio of 1:1, and stored until use. 10 mL of Histoprep (Sigma) was put in a 50 mL tube and 20 mL of the diluted blood was added thereto. The mixture was centrifuged at 3,000 rpm to isolate a white blood cell. 2 mL of the isolated white blood cell was mixed with 6 mL of HBSS and centrifuged at 1,000 rpm. 100 μL of the white blood cell was mixed with 1 mL of Trizole (Life Technology, U.S) to isolate RNA.

Meanwhile, the isolated RNA was diluted with distilled water, and the absorbance at 260 nm was measured to calculate its amount (1.8 μg/μL; Ultraspec 2000 UV-VIS spectrophotometer, GE, U.S). Detailed procedure is as follows:

1 mL of trizole was added to 100 μL of white blood cell, shook well, and left at room temperature for 5 min. Then, 200 μL of chloroform was added, vigorously shook for 15 sec, and left for 3 min. Subsequently, the mixture was centrifuged under a condition of 2~8° C., 15 min and 15,000 rpm, and the supernatant were transferred into a new tube. 500 μL of isopropyl alcohol was added and mixed well, and left at room temperature for 10 min. Then, the mixture was centrifuged at 2~8° C. and 15,000 rpm for 5 min to remove the supernatant. 1 mL of 75% ethanol was added thereto and the mixture was centrifuged under a condition of 2~8° C., 5 min and 15,000 rpm to remove ethanol, and the RNA pellet was dried at room temperature for 5 min. 150 μL of distilled water was added thereto to suspend the RNA pellet, and the absorbance at 260 nm of the suspension was measured. The remnant was stored at −20° C.

EXAMPLE 2

Amplification of Antibody Genes

1 μg of RNA isolated in Example 1 and 1 μL of pd(T)$_{12-18}$ (0.5 μg/μL) were mixed with distilled water to make final volume into 12.5 μL. The mixture was reacted at 70° C. for 2 min and cooled using ices. Then, 5× reaction buffer, 10 mM dNTP mix, recombinant RNase inhibitor and MMLV reverse transcriptase (Clontech, U.S) were added thereto to make final volume into 20 μL, followed by the reaction at 42° C. for 1 hr and at 95° C. for 5 min to synthesize cDNA. PCR reaction was carried out using LiquiMix QM Premix, Magenta (Neurotics Inc, Korea), 4 μL of cDNA as a template, 19 μL of distilled water, and 1 μL of primers designed to homogenously bind to scFv, light chain variable region and light chain variable region (kappa and lambda), respectively. Primers used in PCR and their nucleotide sequences were shown in Table 1.

TABLE 1

Primers used in PCR reaction

| Primers | Nucleotide sequence | SEQ ID NO. |
|---|---|---|
| scFv-Forward | 5'-GTTGTTCCTTTCTATGCGGCCCAGCCGGCCATGGCC-3' | 21 |
| scFv-Reverse | 5'-GAGTCATTCTCGACTTGCGGCCGCACGTTT-3' | 22 |
| scFv-Reverse | 5'-GAGTCATTCTCGACTTGCGGCCGCACC-3' | 23 |
| VH1-Forward | 5'-CAGCCGGCCATGGCCCAGGTGCAGCTGGTGCAGTCTGGG-3' | 24 |
| VH3-Forward | 5'-CAGCCGGCCATGGCCSAGGTGCAGCTGGTGGAGTCTGGG-3' | 25 |
| VH4-Forward | 5'-CAGCCGGCCATGGCCCAGGTGCAGCTGCAGGAGTCGGGC-3' | 26 |
| VH-Reverse | 5'-CGATCCGCCACCTCCGGAGCCACCTCCGCCTGAACCGCCTCCACC-3' | 27 |
| VK1/3A-Forward | 5'-GGTGGCTCCGGAGGTGGCGGATCGGACATCCAGATGACCCAGTCTCCA-3' | 28 |
| VK1/3B-Forward | 5'-GGTGGCTCCGGAGGTGGCGGATCGGAAATTGTGTTGACGCAGTCTCCA-3' | 29 |
| VK2-Forward | 5'-GGTGGCTCCGGAGGTGGCGGATCGGATATTGTGATGACCCAGACTCCACTC-3' | 30 |
| JK_A-Reverse | 5'-TCGACTTGCGGCCGCACGTTTGATWTCCACYTTGGTCCC-3' | 31 |
| JK_B-Reverse | 5'-TCGACTTGCGGCCGCACGTTTGATCTCCASCTTGGTCCC-3' | 32 |
| JK_C-Reverse | 5'-TCGACTTGCGGCCGCACGTTTAATCTCCAGTCGTGTCCC-3' | 33 |
| VL_A-Forward | 5'-GGTGGCTCCGGAGGTGGCGGATCGCAGTCTGYSCTGACTCAGCCACCC-3' | 34 |
| VL_B-Forward | 5'-GGTGGCTCCGGAGGTGGCGGATCGTCCTATGAGCTGACWCAGCCACCC-3' | 35 |
| JL_A-Reverse | 5'-TTCTCGACTTGCGGCCGCACCTAGGACGGTSASCTTGGTCCC-3' | 36 |
| JL_B-Reverse | 5'-TTCTCGACTTGCGGCCGCACCGAGGACGGTCAGCTGGGTGCC-3' | 37 |

PCR reaction was carried out at 95° C. for 5 min, 55° C. for 2 min, 72° C. for 2 min with 30 cycles, finally 72° C. for 15 min.

Figure 1:
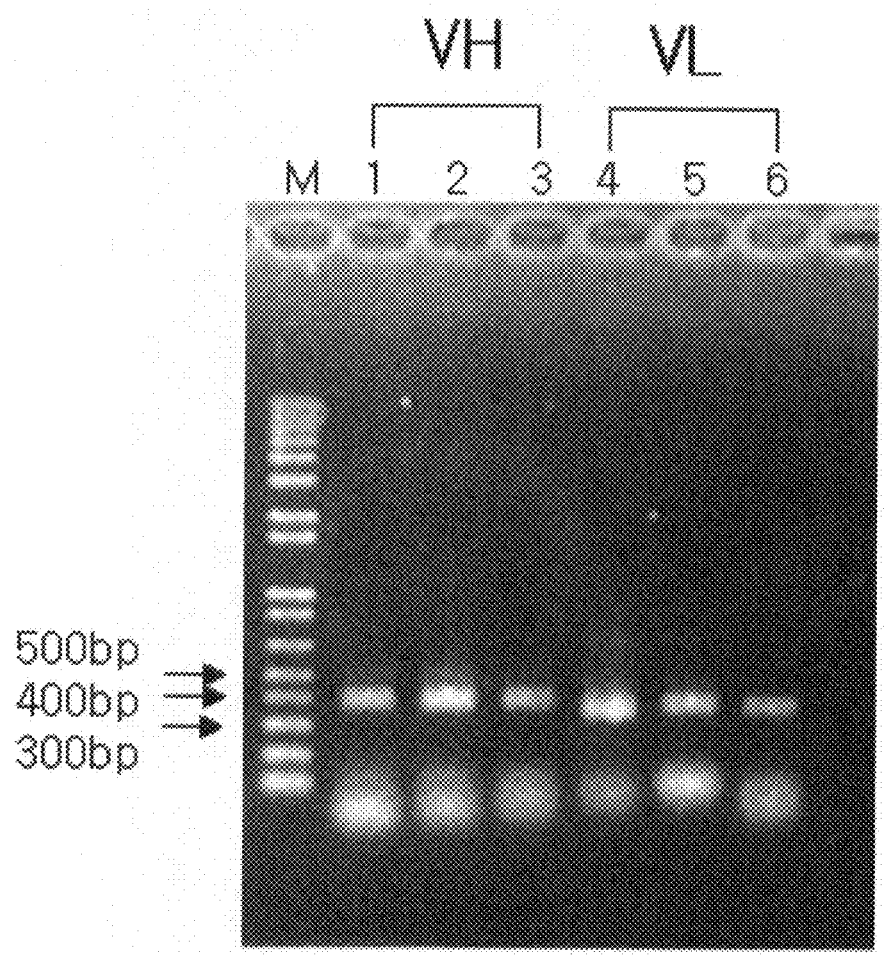
FIG. 1: a photograph of electrophoresis (1% agarose gel) exhibiting DNAs which respectively encode the inventive heavy chain variable (VH) and the light chain variable regions (VL) synthesized by PCR.

The amplified antibody DNAs were identified by an electrophoresis in 1.2% agarose gel (FIG. 1). As shown in FIG. 1, 350 bp of DNA bands specific to the heavy chain and light chain (kappa and lambda) variable regions were obtained. In FIG. 1, M refers to a size marker, VH to heavy chain variable region (lane 1: heavy chain variable region type I; lane 2: heavy chain variable region type III; and lane 3: heavy chain variable region type IV), VL to light chain variable region (lane 4: light chain variable region 1/3 κ; lane 5: light chain variable region 2 κ; and lane 6: light chain variable region λ).

EXAMPLE 3

Restriction Enzyme Digestion of Antibody DNAs

VH and VL (kappa and lambda) prepared in Example 2 were digested with restriction enzymes SfiI/BspEI and BspEI/NotI, respectively, and the digested fragments were isolated from a 1.2% agarose gel and purified using Qiagen kit.

EXAMPLE 4

Ligation of the Antibody DNAs and Preparation of Libraries

Phage-display vector, pKS4H (Green cross Corp., Korea, see Korean Patent No. 0635370), were digested using a restriction enzyme, SfiI/BspEI, and was separated using 1.2% agarose gel electrophoresis, followed by purification using Qiagen kit. 30 µg of the pKS4H was mixed with 3 µg of VH prepared in Example 3, and T4 DNA ligase (New England BioLabs, U.S) was added thereto, followed by the reaction overnight at 25° C. The ligation mixture was purified using Qiagen kit, and was transformed into E. coli XL1-blue (Stratagene, U.S) by electroporation. The transformant was cultured in 100 mL of medium overnight, and the plasmid was isolated. The plasmid was designated as "pKS4H-VH-ΔVL".

Figure 2:
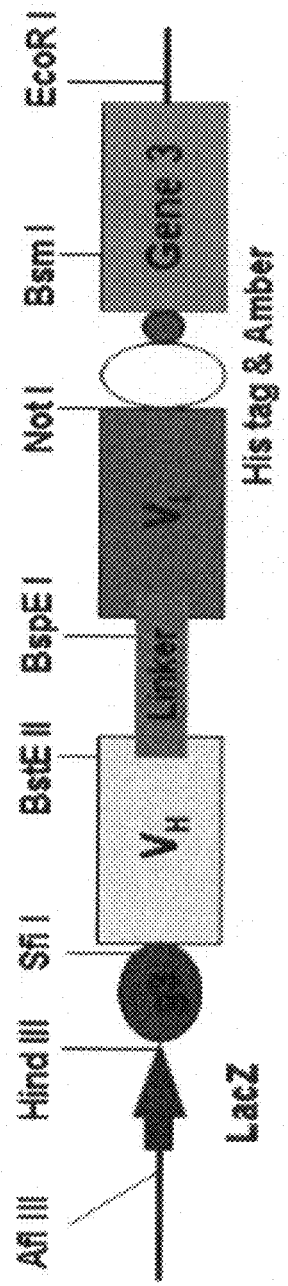
FIG. 2: a cleavage map of the phage-display vector, pKS4H, comprising the heavy chain variable region and the light chain variable region of the inventive antibody.

The plasmid, pKS4H-VH-ΔVL, was digested with a restriction enzyme, BspEI/NotI, and purified as described above. Then, 30 µg of pKS4H-VH-ΔVL plasmid was mixed with 3 µg of VL PCR DNA and T4 DNA ligase (New England BioLabs, U.S), and reacted overnight at 25° C. The ligation mixture was purified using Qiagen kit, and was transformed into E. coli XL1-blue by electroporation. The transformant was cultured in 100 mL of medium containing carbenicillin and tetracyclin at 37° C. for 2 hours. Then, M13 helper phage (Stratagene, U.S) was inoculated to the medium and cultured for 16 hr to prepare a phage library as reported in Engberg et al (Mol. Biotechnol., 6, 287-310, 1995). Meanwhile, a plasmid was isolated from the E. coli, and designated as "pKS4H-VH-VL". The cleavage map of the plasmid is depicted in FIG. 2.

EXAMPLE 5

Selection of Antibodies Binding to the Epidermal Growth Factor Receptor

Figure 3:
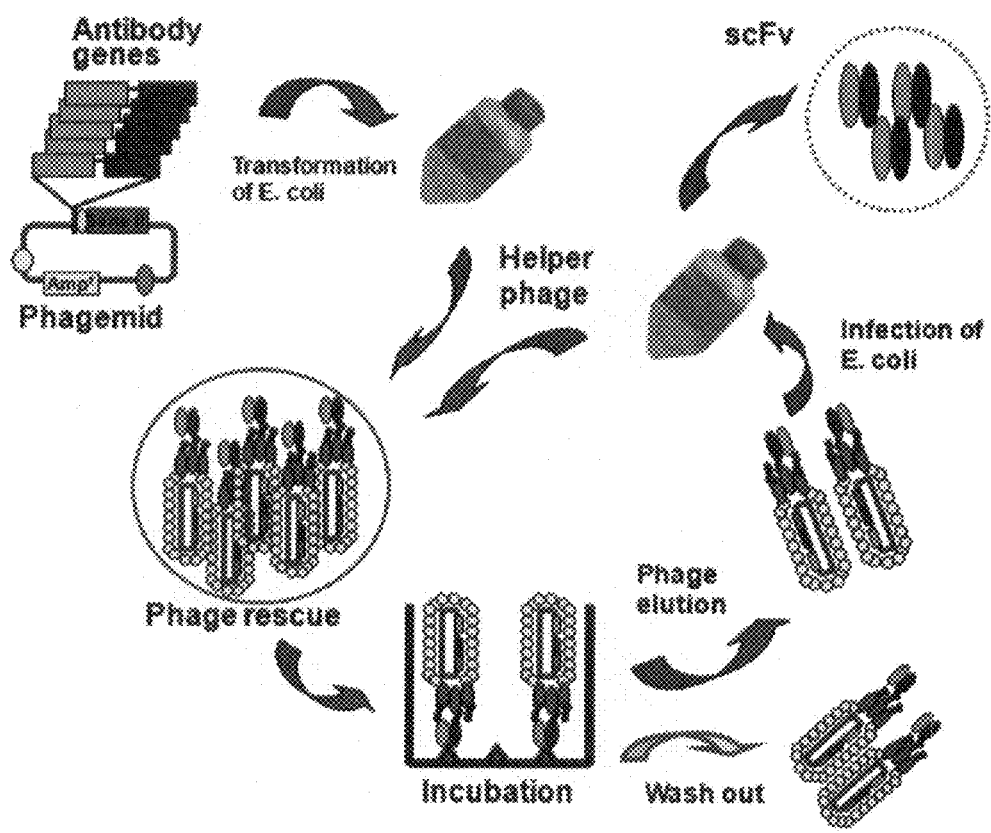
FIG. 3: a diagram showing a process of selecting an antibody from an antibody library using the biopanning technique.

Antibodies binding to EGFR were selected by a modification of panning technique (Engberg et al., Mol. Biotechnol., 6, 287-310, 1996; and Kim et al., Gene, 241, 19-25, 2000). Specifically, EGFR (Sigma, U.S) was diluted with PBS and coated onto each immunotube (NUNC, Denmark). Then, the phage library prepared in Example 4 was added to the coated immunotube and reacted. Phages binding to EGFR were detached using 0.1M of glycine buffer (pH 2.0). Subsequently, E. coli XL1-blue was infected with the phages and a helper phage was added. The E. coli was incubated overnight and PEG solution containing 20% PEG 8,000 and 15% NaCl was added thereto. Then, precipitated phages were collected (phage rescue). The phages were again reacted to the EGFR-coated immunotube and the procedure was repeated 4 times (panning). Through the procedure, human antibodies ER2 and ER79 were selected as antibodies binding to EGFR. The process of selecting antibodies using phage-display libraries was depicted in FIG. 3.

Each colony of libraries completed 4 times panning was incubated in 2 mL of medium, according to the known method (Kim et al., Gene, 241, 19-25, 2000), and expression of antibody was induced by treatment of IPTG (isopropyl β-D-1-thiogalactopyranoside). The induction of antibody was measured by ELISA (Enzyme-Linked ImmunoSorbent Assay) using an EGFR coated 96-well plate.

EXAMPLE 6

Sequence Analysis of Selected Antibodies

Figure 4:
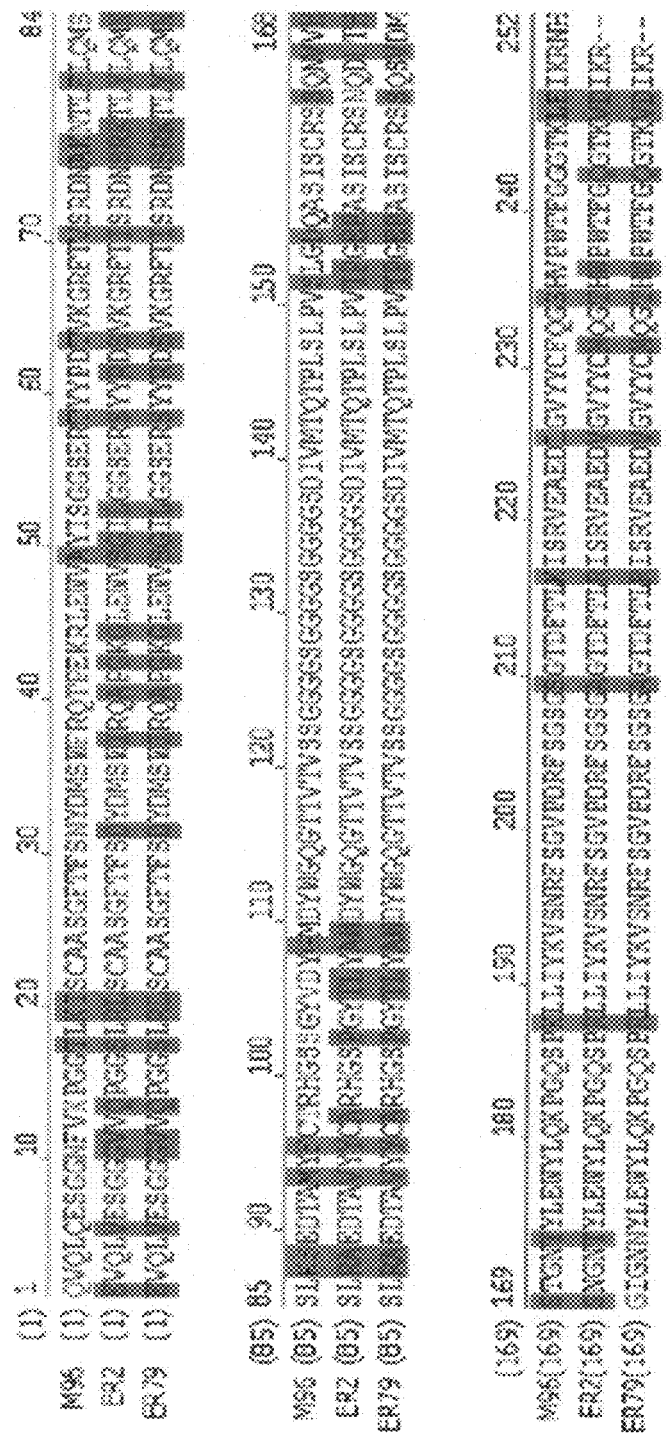
FIG. 4: amino acid sequences of the single chain variable fragments (scFv) of the inventive antibodies, ER2 and ER79.

Colonies which secrete human antibodies ER2 and ER79 selected in Example 5 were incubated overnight in 10 mL of LB medium containing 50 µg/mL of carbenicillin and recombinant plasmids were isolated using Qiagen plasmid mini kit (Qiagen, Valencia, Calif., U.S) therefrom. The plasmids were digested with SfiI/NotI, identified of the insertion of fragments of antibodies by an electrophoresis in agarose gel. The DNA sequence of scFv inserted into the plamid was analyzed.

p033 of SEQ ID NO: 38 was used as a sequencing primer, and sequences were analyzed in Genotech (Daejeon, Korea) according to the conventional method. The DNA sequences of scFv of ER2, ER79 and M96 (mouse antibody) were translated into amino acids using a web-based program (www.expasy.org: DNA to Protein translate tool), and the translated amino acid sequences were shown in FIG. 4. In FIG. 4, M96, ER2 and ER79 refer to amino acid of scFv of M96 (mouse antibody) and ER2 and ER79 of the present invention, respectively. As shown in FIG. 4, human antibodies ER2 and ER79 had different amino acid sequence.

EXAMPLE 7

Construction of Expression Vectors

In order to convert the antibody fragments into intact immunoglobulins, antibody expression vectors, pRC13 and pKC12 (plasmids for insertion of a variable region of a human antibody against the surface antigen of hepatitis B virus; Korean Patent No. 523732; Deposit No. KCLRF-BP-00054) were used. The vectors of pRC13 and pKC12 are introduced into a hybridoma HBAb-49 and deposited on Nov. 30, 2001 at the Cancer Research Institute Seoul National University of 28 Yongon-dong, Chongno-gu, Seoul 110-744, Korea under the Budapest Treaty on the International Recognition of the Deposit of Microorganisms for the Purpose of Patent Procedure, under Accession No. KCLRF-BP-00054.

Each VH fragment was inserted into HindIII and ApaI site of the heavy chain expression vector, pRC13. As exemplified in FIG. 5, the DNA encoding the heavy chain variable regions (VHs) of the human antibody ER2 (SEQ ID NO: 7) and the DNA encoding the heavy chain variable regions (VHs) of the human antibody ER79 (SEQ ID NO: 7) were amplified by PCR using respective primer of SEQ ID NOs: 39 and 40, digested with HindIII/IApaI, and inserted into pRC13 which was digested with same restriction enzymes. The recombinant vector was designated "ER2-Heavy-pRC13" or "ER79-Heavy-pRC13". The primers used are shown in Table 2.

TABLE 2

Primers used in PCR

| Primers | Nucleotide sequence | SEQ ID NO |
|---|---|---|
| VH-Forward | 5'-GGAGACCCAAGCTTGGTACCGAGCTCGGAT CCACTAGTAACGGCCGCCAGTGTGCTGGAA-3' | 39 |
| VH-Reverse | 5'-GAAGACCGATGGGCCCTTGGTGGAGGCTGA GGAGACGGTGAC-3' | 40 |

Meanwhile, each VL fragment was inserted into NheI and ApaI site of the light chain expression vector, pKC12. As exemplified in FIGS. 6 and 7, each of the DNA encoding the light chain variable region (VL) of the human antibody ER2 (SEQ ID NO: 8) and the DNA encoding the light chain variable region (VL) of the human antibody ER79 (SEQ ID NO: 10) was amplified by PCR using respective primer of SEQ ID NOs: 41 and 42, digested with NheI/ApaI, and inserted into pKC12 which was digested with same restriction enzymes. The recombinant vector was designated "ER2-Light-pKC12" or "ER79-Light-pKC12". The primers used are shown in Table 3.

TABLE 3

Primers used in PCR

| Primers | Nucleotide sequence | SEQ ID NO |
|---|---|---|
| VL-Forward | 5'-TAGGGAGACCCGCTAGCGGAGCAAGATGGA TTCACAGGCCCAGGT-3' | 41 |
| VL-Reverse | 5'-TATAGAATAGGGCCCCCCCTCGAGGTCGAC CTAACACTCTCCCCT-3' | 42 |

EXAMPLE 8

Construction of Animal Cell Lines Secreting Antibodies $2 \times 10^5$ CHO (Chinese hamster ovary) cells were incubated in T-25 flask (NUNC, Denmark) filled with α-MEM medium (Life Technologies, U.S) containing 10% FBS (Life Technologies, U.S), 24 hours prior to transformation. The incubation was carried out in 37° C. incubator in the presence of 5% $CO_2$, until confluency reaches 50%. Next day, 30 μg of lipofectin (Life Technologies, U.S) was added to 1.5 mL of opti-MEM (Life Technologies, U.S) and left undisturbed at room temperature for 90 min. After 90 min, the medium was mixed with the medium containing ER2-Heavy-pRC13, ER2-Light-pKC12, ER79-Heavy-pRC13 and ER79-Light-pKC12, respectively, to react at room temperature for 15 min. During the reaction, cells for transformation was separated from the medium, and washed three times with PBS. To the washed cells, the reaction mixture was added for incubation. After 6 hours, the reaction mixture was removed, and α-MEM medium was added for incubation for 48 hours. The cells incubated for 48 hours were treated with trypsin (Life Technologies, U.S) to detach from the flask, diluted with α-MEM medium, and subcultured at 96-well plate (NUNC, Denmark). At the time, the α-MEM medium does not contain ribonucleoside and deoxyribonucleoside, while contains 10% of dialyzed FBS (Life Technologies, U.S) and 550 μg/mL of G418 (Sigma, U.S). The medium was replaced with a new medium every two days. The culture supernatant forming colonies was collected for ELISA, and selected cells were transferred into 12-well plate. The cells were transferred into 6-well plate if the cells grow well in 12-well plate, and methotrexate (MTX, Choongwae Pharma Corporation, Korea) was treated if the cells grow well in 6-well plate. The initial concentration of MTX was 20 nM, and increased to 80 nM, 320 nM and 1 μM according to the cell's growth. Cell lines which survived at a concentration of 1 μM and had a high antibody secretion amount were selected, and mass-cultured. The mass culture was carried out in an incubator with 65 rpm, 5% $CO_2$ and 37° C., using spinner flask and serum-free medium. The cell lines ($10^8$ cells) were cultured in 250 mL flask filled with 100 mL of serum-free medium. When the number of the cells became 2 times higher, supernatant and cells were collected by centrifugation at 1,000 rpm for 5 min, respectively. The collected cells were cultured again in 500 mL flask filled with 200 mL of medium. When the number of the cells became 2 times higher, cells were separated and transferred into 3 L spinner flask filled with 1 L of medium. Sodium butyrate (Aldrich, U.S) were added thereto to a final concentration of 2 mM, the cells were cultured for 5 days, and the supernatant was collected from the medium. From all supernatants collected by culturing in spinner flasks, antibodies were purified using a protein A-agarose column (Amersham Pharmacia Biotech, U.S) and were analyzed using SDS-PAGE electrophoresis.

Figure 8:
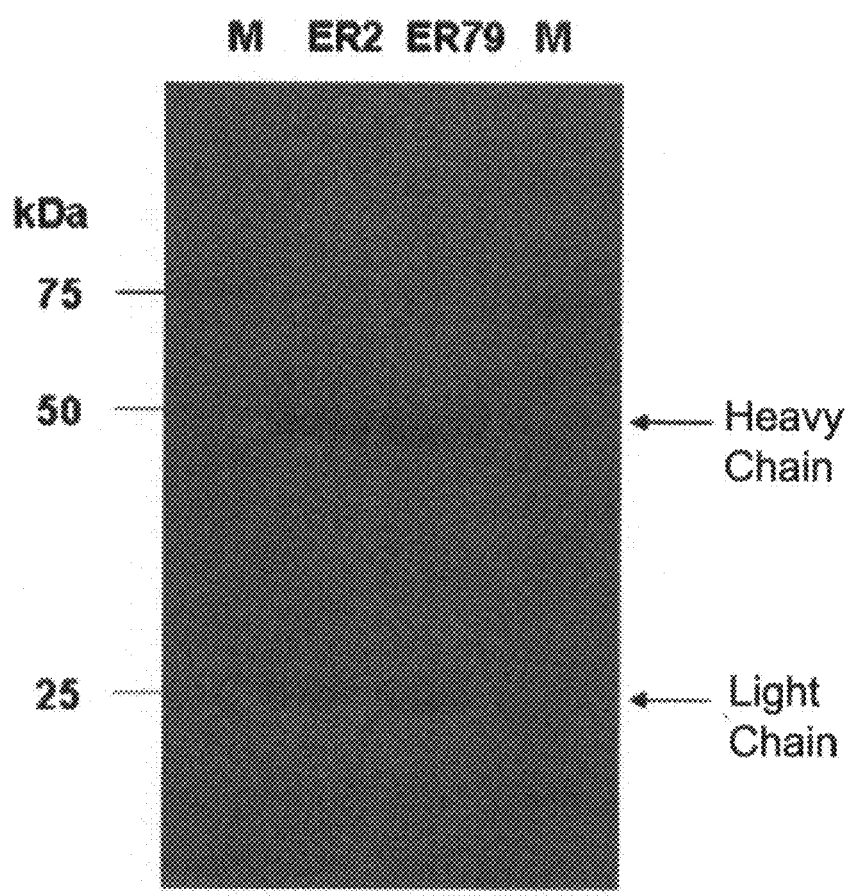
FIG. 8: SDS-PAGE results obtained for the heavy chain and light chain expressed from the transformant.

As shown in FIG. 8, about 50 kd of heavy chain band and 25 kd of light chain band were observed, indicating that antibodies were certainly produced.

EXAMPLE 9

Measurement of Antibody Affinity

The affinities of the antibodies obtained in Example 8 to EGFR were determined by a competitive ELISA method (Kim et al., *Hybridoma*, 20, 265-272, 2001), and the results were shown in FIG. 9. Brief procedure is as follows:
(1) Determination of Optimum Concentration of Antibodies
A. Preparation of a Plate
  100 μL of EGFR (Sigma, U.S) at a 2 μg/mL dilution in PBS was added to each well of a plate and incubated overnight at 4° C. Each well of the plate was washed once with PBST, 300 μL of 1% BSA-PBS solution was added to each well, and stored for 1 hour at room temperature.
B. $1^{st}$ Reaction
  100 μL of each purified antibody (0.5 μg/mL) was added to each well of plate, reacted for 2 hours at room temperature, and washed four times with PBST.
C. $2^{nd}$ Reaction
  100 μL of goat anti-human IgG (Fab specific)-perxoidase conjugate (Sigma) at a 1:5000 dilution in 1% BSA-PBS was added to each well, incubated for 1 hour at room temperature, and washed four times with PBST.
D. Substrate Reaction
  100 μL of TMB (3,3',5,5'-tetramethylbenzidine, Microwell peroxidase substrate system (KPL, MD, U.S)) was added to each well and O.D value was measured at 405 nm. Optimum concentrations of antibodies were determined as ½ of concentrations at which maximum binding appears.
(2) Competitive ELISA
A. Preparation of a Plate
  100 μL of EGFR (Sigma, U.S) at a 2 μg/mL dilution in PBS was added to each well of a plate and incubated overnight at 4° C. Each well was washed once with PBST, 300 μL of 1% BSA-PBS solution was added to each well, and stored for 1 hour at room temperature.

B. 1st Reaction

2 μg of EGFR was diluted by a two-fold and 10 μL of the diluted EGFR was added to each well of the plate. Then, 90 μL of the antibody diluted to the optimum concentration determined in (1) was added to each well, incubated for 2 hours at room temperature, and washed 4 times with PBST.

C. 2nd Reaction 100 μL of goat anti-human IgG (Fab specific)-perxoidase conjugate (Sigma) at a 1:5000 dilution in 1% BSA-PBS was added to each well, incubated for 1 hour at room temperature, and washed four times with PBST.

D. Substrate Reaction

100 μL of TMB (3,3',5,5'-tetramethylbenzidine, Microwell peroxidase substrate system (KPL, MD, U.S)) was added to each well and O.D value was measured at 405 nm. Concentration of EGFR which inhibits 50% of maximum binding (O.D value in which no competing EGFR exists) was determined as Kd.

As shown in FIG. 9, the human antibody ER2 showed a similar affinity and ER79 showed about 63% of affinity, relative to those of a chimeric antibody (C225) and a mouse antibody (M96). Further, the affinities of the inventive antibodies were higher than those of ER414 (human antibody prior to biopanning).

EXAMPLE 10

Figure 10:
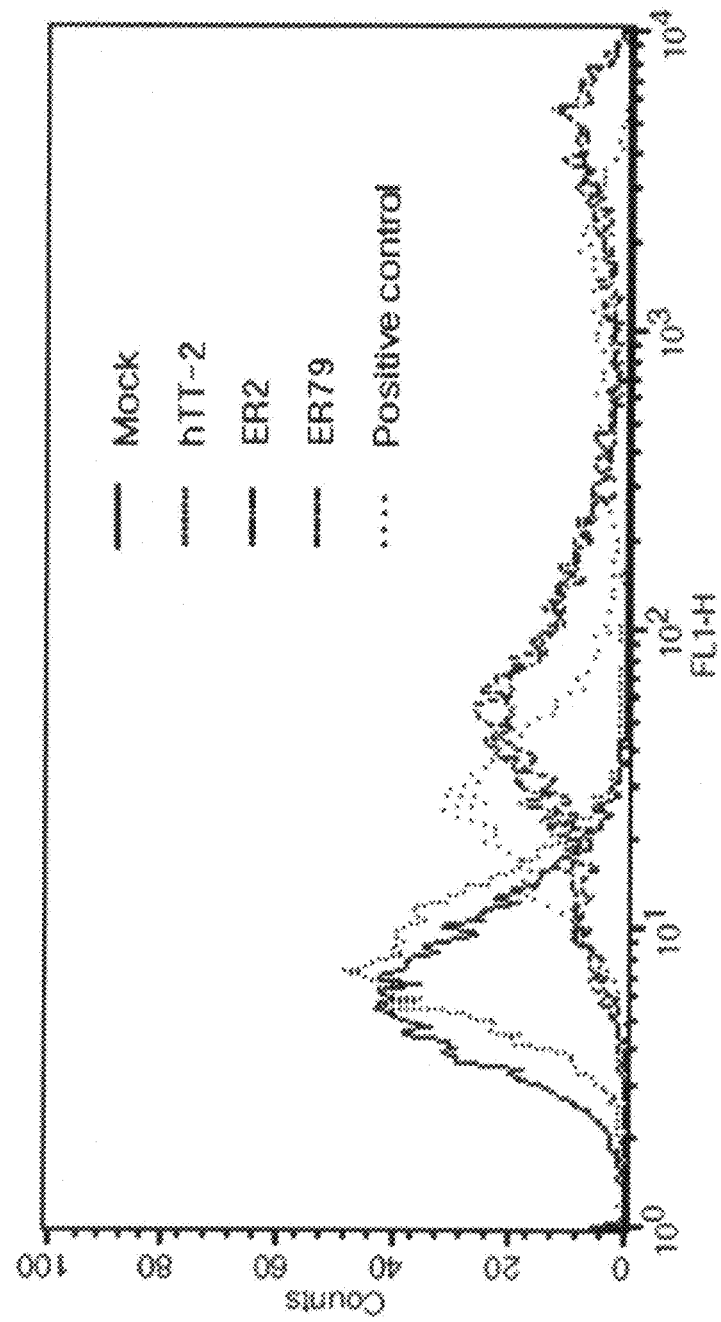
FIG. 10: a flow cytometer exhibiting the binding of the inventive antibodies with the epidermal growth factor receptor overexpressed in a cancer cell line (A431)

Verification of the Binding of the Inventive Antibodies to EGFR in a Tumor Cell Line In order to verify that the inventive antibodies, ER2 and ER79, bind to EGFR overexpressed in a tumor cell line, a flow cytometry was used. Briefly, A431 cells (Deposit No. KCLB 80005), an epidermoid carcinoma cell line which overexpresses EGFR, were washed with 1% BSA-PBS. The washed cells ($1 \times 10^6$ cells) were incubated with 10 μg of the inventive antibodies for 2 hours at 4° C. and washed two times with 1% BSA-PBS. Mock (without antibody) and hTT-2 (anti-tetanus monoclonal antibody; 10 μg; Green cross incorporation; Korean Patent No. 0624011) were used as negative controls, and M96 (mouse anti-EGFR; 10 μg) as a positive control. FITC-labeled goat anti-mouse (Fab-specific) conjugate was added to the antibody cell solution and incubated for 40 minutes on ice. The cells were washed two times with 1% BSA-PBS and suspended in 1 mL of 1% BSA-PBS to be analyzed using flow cytometry (FACS Calibur, BD Bioscience). The results are shown in FIG. 10. These results indicate that the inventive antibodies, ER2 and ER79, bind to EGFR in A431 cells, while hTT2 (anti-tetanus monoclonal antibody) does not bind.

EXAMPLE 11

Effect of the Inventive Antibodies on EGFR Phosphorylation

The inventive antibodies, ER2 and ER79, were tested for their ability to inhibit the EGFR phosphorylation. Briefly, MDA-MB-231 cells (Deposit No. KCLB 30026), a breast cancer cell line, were incubated in 24-well plates (NUNC) at a cell concentration of $1 \times 10^5$. Two days later, the inventive antibodies were added to each well, in amounts of 5, 25, 50, and 100 μg, respectively, and then 50 ng of EGF was added to each well and incubated for 30 minutes. For comparison, M96 antibody (Green cross incorporation, Korea; see Korean Patent No. 0680141), C225 antibody (trade name: Erbitux; ImClone, U.S), and ER 414 antibody were used instead of the inventive antibodies. Cell extracts were prepared using 0.5 mL of lysis buffer (10 mM Tris, 150 mM NaCl, 5 mM EDTA, 1% Triton X-100, 1 mM sodium orthovanadate) per well. The cell extracts were subjected to SDS-PAGE electrophoresis, and separated proteins were electrotransferred into a nitrocellulose membrane. The membrane was blocked for 30 minutes using 5% BSA solution in order to reduce non-specific binding of the transferred proteins, and immunoblotted overnight at 4° C. using anti-phosphotyrosine specific peroxidase conjugate (Zymed, U.S) which specifically reacts with phosphorylated EGFR. The immunoblotted membrane was washed with PBS containing 0.05% tween and developed using a substrate of 0.018% (v/v) 4-chloro-1-naphthol and 0.045% hydrogen peroxide in PBS and methanol. The results were shown in FIG. 11. These results indicate that the amounts of antibodies affect the EGFR phosphorylation and ER2 and ER79 have similar inhibitory abilities of EGFR phosphorylation compared to the positive control group treated with Erbitux.

EXAMPLE 12

Identification of Binding Sites of the Antibodies to EGFR

In order to check if the inventive antibodies, ER2 and ER79, has the same binding sites to EFGR with a chimeric antibody C225 (Erbitux, ImClone, U.S), a surface plasmon resonance technology (SPR; Biacore 2000) was used. EGFR antigen was immobilized onto a carboxymethylated dextran surface chip (CM5 chip, Pharmacia) in response units of about 1,000. Then, C225 antibody was injected over the chip, and ER2 and ER79 were immediately injected without dissociation between the antigens and antibodies, respectively, followed by measurement of the binding reaction at 25° C. The results were shown in FIG. 12. The inventive human antibodies were shown to have different binding sites with C225 antibody.

While the invention has been described with respect to the above specific embodiments, it should be recognized that various modifications and changes may be made to the invention by those skilled in the art which also fall within the scope of the invention as defined by the appended claims.

What is claimed is:

1. An antibody which specifically binds to the epidermal growth factor receptor (EGFR), comprising:
   a) a heavy chain variable region comprising complementarity determining regions (CDRs) 1, 2, and 3 having the amino acid sequences of SEQ ID NOs: 1, 2, and 3, respectively;
   b) a light chain variable region comprising CDR 1, CDR 2, and CDR 3 having the amino acid sequences of SEQ ID NOs: 4, 5, and 6, respectively;
   c) a heavy chain constant region; and
   d) a light chain constant region.

2. The antibody of claim 1, comprising:
   a) a heavy chain variable region having the amino acid sequence of SEQ ID NO:7;
   b) a light chain variable region having the amino acid sequence of SEQ ID NO:8;
   c) a heavy chain constant region; and
   d) a light chain constant region.

3. An antibody which specifically binds to the epidermal growth factor receptor (EGFR), comprising:
   a) a heavy chain variable region comprising CDR 1, CDR 2, and CDR 3 having the amino acid sequences of SEQ ID NOs: 1, 2, and 3, respectively;
   b) a light chain variable region comprising CDR 1, CDR 2, and CDR 3 having the amino acid sequences of SEQ ID NOs: 9, 5, and 6, respectively;
   c) a heavy chain constant region; and
   d) a light chain constant region.

4. The antibody of claim 3, comprising:
   a) a heavy chain variable region having the amino acid sequence of SEQ ID NO:7;
   b) a light chain variable region having the amino acid sequence of SEQ ID No:10;
   c) a heavy chain constant region; and
   d) a light chain constant region.

5. The antibody of any one of claims 1-4, wherein the antibody is a humanized antibody.

6. The antibody of any one of claims 1-4, wherein the antibody blocks the signal transduction induced by the epidermal growth factor (EGF).

7. A DNA encoding an antibody heavy chain variable region comprising CDR 1, CDR 2, and CDR 3 having the amino acid sequences of SEQ ID NOs: 1, 2, and 3, respectively.

8. The DNA of claim 7, wherein the DNA comprises the polynucleotide having the nucleotide sequence of SEQ ID NO: 11 encoding the amino acid sequence of SEQ ID NO: 1, the polynucleotide having the nucleotide sequence of SEQ ID NO: 12 encoding the amino acid sequence of SEQ ID NO: 2, and the polynucleotide having the nucleotide sequence of SEQ ID NO: 13 encoding the amino acid sequence of SEQ ID NO: 3.

9. A DNA encoding an antibody heavy chain variable region having the amino acid sequence of SEQ ID NO: 7.

10. The DNA of claim 9, wherein the DNA comprises the polynucleotide having the nucleotide sequence of SEQ ID NO: 14 encoding the amino acid sequences of SEQ ID NO: 7.

11. A DNA encoding an antibody light chain variable region comprising CDR 1, CDR 2, and CDR 3 having the amino acid sequences of SEQ ID NOs: 4, 5, and 6, respectively.

12. The DNA of claim 11, wherein the DNA comprises the polynucleotide having the nucleotide sequence of SEQ ID NO: 15 encoding the amino acid sequence of SEQ ID NO: 4, the polynucleotide having the nucleotide sequence of SEQ ID NO: 16 encoding the amino acid sequence of SEQ ID NO: 5, and the polynucleotide having the nucleotide sequence of SEQ ID NO: 17 encoding the amino acid sequence of SEQ ID NO: 6.

13. A DNA encoding an antibody light chain variable region having the amino acid sequences of SEQ ID NO: 8.

14. The DNA of claim 13, wherein the DNA comprises the polynucleotide having the nucleotide sequence of SEQ ID NO: 18 encoding the amino acid sequences of SEQ ID NO: 8.

15. A DNA encoding an antibody light chain variable region comprising CDR 1, CDR 2, and CDR 3 having the amino acid sequences of SEQ ID NOs: 9, 5, and 6, respectively.

16. The DNA of claim 15, wherein the DNA comprises the polynucleotide having the nucleotide sequence of SEQ ID NO: 19 encoding the amino acid sequence of SEQ ID NO: 9, the polynucleotide having the nucleotide sequence of SEQ ID NO: 16 encoding the amino acid sequence of SEQ ID NO: 5, and the polynucleotide having the nucleotide sequence of SEQ ID NO: 17 encoding the amino acid sequence of SEQ ID NO: 6.

17. A DNA encoding an antibody light chain variable region having the amino acid sequences of SEQ ID NO: 10.

18. The DNA of claim 17, wherein the DNA comprises the polynucleotide having the nucleotide sequence of SEQ ID NO: 20 encoding the amino acid sequences of SEQ ID NO: 10.

19. An expression vector for expressing the heavy chain variable region of the antibody specifically binding to the epidermal growth factor receptor (EGFR), comprising the DNA of claim 7.

20. The expression vector of claim 19, wherein the vector is ER2-Heavy-pRC13 or ER79-Heavy-pRC13 whose cleavage map is shown in FIG. 5.

21. An expression vector for expressing the light chain variable region of the antibody specifically binding to the epidermal growth factor receptor (EGFR), comprising the DNA of claim 11.

22. The expression vector of claim 21, wherein the vector is ER2-Light-pKC12 whose cleavage map is shown in FIG. 6.

23. An expression vector for expressing the light chain variable region of the antibody specifically binding to the epidermal growth factor receptor (EGFR), comprising the DNA of claim 15.

24. The expression vector of claim 23, wherein the vector is ER79-Light-pKC12 whose cleavage map is shown in FIG. 7.

25. An animal cell line transformed with an expression vector for expressing a heavy chain variable region of the antibody which specifically binds to the epidermal growth factor receptor (EGFR), comprising a first DNA encoding an antibody heavy chain variable region and an expression vector for expressing a light chain variable region of the antibody specifically binding to the epidermal growth factor receptor (EGFR), comprising a second DNA encoding an antibody light chain variable region,
    wherein the first DNA encodes an antibody heavy chain variable region comprising CDR 1, CDR 2, and CDR 3 having the amino acid sequences of SEQ ID NOs: 1, 2, and 3, respectively, and
    wherein the second DNA encodes an antibody light chain variable region comprising CDR 1, CDR 2, and CDR 3 having the amino acid sequences of SEQ ID NOs: 4, 5, and 6, respectively.

26. The animal cell line of claim 25, wherein the animal cell line is CHO (Chinese hamster ovary), HEK 293, or NSO cell line.

27. An animal cell line transformed with an expression vector for expressing a heavy chain variable region of the antibody which specifically binds to the epidermal growth factor receptor (EGFR), comprising a first DNA encoding an antibody heavy chain variable region and an expression vector for expressing a light chain variable region of the antibody specifically binding to the epidermal growth factor receptor (EGFR), comprising a second DNA encoding an antibody light chain variable region,
    wherein the first DNA encodes an antibody heavy chain variable region comprising CDR 1, CDR 2, and CDR 3 having the amino acid sequences of SEQ ID NOs: 1, 2, and 3, respectively, and
    wherein the second DNA encodes an antibody light chain variable region comprising CDR 1, CDR 2, and CDR 3 having the amino acid sequences of SEQ ID NOs: 9, 5, and 6, respectively.

28. The animal cell line of claim 27, wherein the animal cell line is CHO (Chinese hamster ovary), HEK 293, or NSO cell line.

29. A composition for treating a cancer, comprising the antibody of claim 1 or 3 and a pharmaceutically acceptable carrier.

30. The composition of claim 29, which further comprises at least one chemotherapeutic agent selected from the group consisting of cisplatin, gemcitabine, doxorubicin, 5-FU, irrinotecan, and paclitaxel.

\* \* \* \* \*